United States Patent [19]  [11] Patent Number: 5,071,844
Alker et al.  [45] Date of Patent: Dec. 10, 1991

[54] 5,11-DIHYDRODIBENZO[B,E][1,4]-THIAZE-PINES USEFUL AS GASTRO INTESTINAL SELECTIVE CALCIUM ANTAGONISTS

[75] Inventors: David Alker; Robert J. Bass, both of Birchington; Peter E. Cross, Canterbury, all of England

[73] Assignee: Pfizer Inc., New York, N.Y.

[21] Appl. No.: 527,616

[22] Filed: May 23, 1990

[30] Foreign Application Priority Data

May 27, 1989 [GB] United Kingdom ............... 8912303

[51] Int. Cl.$^5$ ................ C07D 417/06; C07D 417/14; A61K 31/55
[52] U.S. Cl. .................................... 514/211; 540/550; 540/596; 540/609; 546/268; 546/334; 548/517; 548/575
[58] Field of Search .................. 540/550; 514/211

[56] References Cited

U.S. PATENT DOCUMENTS 3,188,322  6/1965  Yale et al. .................... 260/327

FOREIGN PATENT DOCUMENTS 407127  8/1966  Switzerland .
774882  5/1957  United Kingdom .
975705  3/1961  United Kingdom .
988008  3/1965  United Kingdom .

OTHER PUBLICATIONS

Yale, Harry L. et al., "Novel Polycyclic Heterocycles., Derivatives of 5,11-Dihydrodibenz[b,e][1,4]oxazepine and 5,11-Dihydrodibenzo[b,e][1,4]thiazepine, J. of Medicinal Chem.", vol. 13, No. 4 (1970), pp. 713-722.
Goodman and Gilman's *The Pharmacological Basis of Therapeutics*, 7th Ed., (1985), p. 141.

Primary Examiner—Mukund J. Shah
Assistant Examiner—Philip I. Datlow
Attorney, Agent, or Firm—Peter C. Richardson; J. Trevor Lumb; A. Dean Olson

[57] ABSTRACT

The invention provides compounds of the formula:

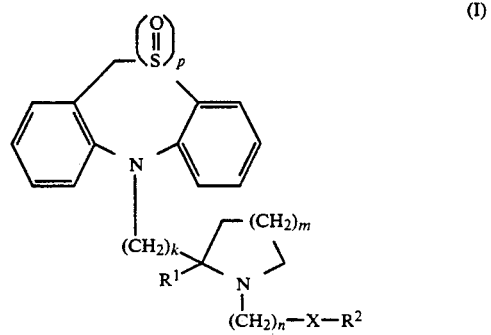

wherein
k is 1, 2 or 3;
m is 1, 2 or 3;
n is 1, 2 or 3;
p is 0, 1 or 2;
X is O, S or a direct link, with the proviso that when X is O or S, n is 2 or 3;
$R^1$ is H or $C_1$-$C_4$ alkyl; and
$R^2$ is an optionally substituted phenyl or heteroaryl group; and
pharmaceutically acceptable salts thereof.

These compounds are useful for the treatment of motility disorders, particularly those of the gut such as irritable bowel syndrome.

18 Claims, No Drawings

5,11-DIHYDRODIBENZO[B,E][1,4]-THIAZEPINES USEFUL AS GASTRO INTESTINAL SELECTIVE CALCIUM ANTAGONISTS

TECHNICAL FIELD

This invention relates to 5,11-dihydrodibenzo[b,e][1,4]thiazepines, specifically to certain 5,11-dihydro-5-(1-substituted-2-pyrrolidinyl-, piperidinyl- or perhydroazepinylalkyl)dibenzo[b,e][1,4]thiazepines which are gastro-intestinal(GI) selective calcium antagonists. These dihydrodibenzothiazepines are particularly useful in the treatment of motility disorders, particularly those of the gut such as irritable bowel syndrome(IBS).

BACKGROUND OF THE INVENTION

The compounds of the present invention are potent inhibitors of intestinal motility in both the small and large bowel, being calcium antagonists with well defined selectivity for the gastrointestinal tract.

Irritable bowel syndrome is a motility disorder characterised by altered bowel habit (i.e. constipation and/or diarrhoea), distension and abdominal pain. The calcium antagonists of the present invention reduce the motility of the gut thus having an antispasmodic effect on the bowel without affecting blood pressure or other cardiac parameters. The compounds of the invention are also useful in the treatment of other conditions where spasm or hypermotility of smooth muscle tissue is involved. Such conditions involve the smooth muscle of the gastro-intestinal tract, uterus, ureter and biliary tract and include diseases such as oesophageal dysmotility, gastro-oesophageal reflux disease, achalasia, functional bowel disease, pseudo-obstructive disease, non-cardiac chest pain, diverticular disease, inflammatory bowel disease, dysmenorrhea, pre-term labour, incontinence, uteric colic and biliary spasm. They are also of use in the radiological examination of the gut.

SUMMARY OF THE INVENTION

According to the present invention, there are provided compounds of the formula:

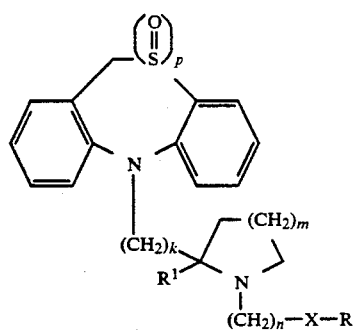

(I)

wherein
k is 1, 2 or 3;
m is 1, 2 or 3;
n is 1, 2 or 3;
p is 0, 1 or 2;
X is O, S or a direct link, with the proviso that when X is O or S, n is 2 or 3;
$R^1$ is H or $C_1$–$C_4$ alkyl; and
$R^2$ is
(a)

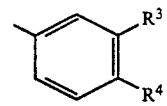

wherein $R^3$ and $R^4$ are each independently selected from H, $C_1$–$C_4$ alkyl, $C_1$–$C_4$ alkoxy, —OH, —N($C_1$–$C_4$ alkyl)$_2$, halo and —$CF_3$;

(b)

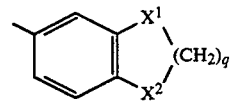

wherein
q is 1, 2 or 3; and
$X^1$ and $X^2$ are each independently selected from O and —$CH_2$—; or (c) a pyridinyl, pyridazinyl, pyrimidinyl, pyrazinyl or thienyl group, said group being optionally substituted by up to 2 substituents each independently selected from $C_1$–$C_4$ alkyl and $C_1$–$C_4$ alkoxy, and pharmaceutically acceptable salts thereof.

"Halo" means F, Cl, Br and I. "Halo" is preferably chloro.

$C_3$ and $C_4$ alkyl and alkoxy groups may be straight or branched chain. The preferred alkyl and alkoxy groups are methyl and methoxy.

In the above definition of compounds of the formula (I):
Preferably, k is 1 or 2.
Most preferably, k is 1.
Preferably, m is 1 or 2.
Most preferably, m is 1.
Preferably, n is 2.
Preferably, p is 0.
Preferably, X is a direct link.
Preferably, $R^1$ is H or methyl.
Most preferably, $R^1$ is H.
Preferably, $R^2$ is
(a)

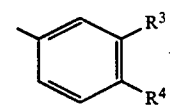

wherein $R^3$ and $R^4$ are each independently selected from H, $C_1$–$C_4$ alkyl, $C_1$–$C_4$ alkoxy, —OH and halo;

(b)

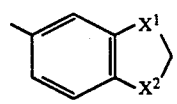

wherein $X^1$ and $X^2$ are as previously defined for a compound of the formula (I); or
(c) pyridinyl, pyrimidinyl or thienyl group, said group being optionally substituted by up to 2 substituents each independently selected from $C_1$–$C_4$ alkyl and $C_1$–$C_4$ alkoxy.

More preferably, $R^2$ is (a)

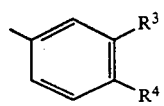

wherein $R^3$ and $R^4$ are each independently selected from H, —$CH_3$, —$OCH_3$, —OH and Cl;

(b)

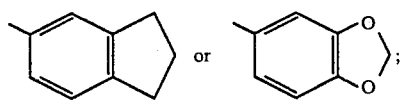

or (c) a pyridinyl, pyrimidinyl or thienyl group.

Yet more preferably, $R^2$ is phenyl, 3-methylphenyl, 4-methylphenyl, 4-hydroxyphenyl, 4-methoxyphenyl, 3,4-dimethoxyphenyl, 4-chlorophenyl, 5-indanyl, 3,4-methylenedioxyphenyl, 2-pyridinyl, 4-pyrimidinyl or 3-thienyl.

Most preferably, $R^2$ is 4-methoxyphenyl.

The numbering of the 5,11-dihydrodibenzo[b,e][1,4]thiazepine ring system and the position of the asymmetric centres (*) within the compounds of the formula (I) are as indicated below:

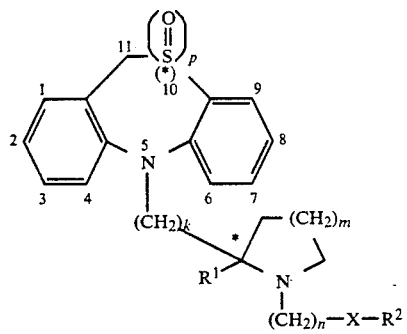

(I)

wherein (*) indicates an asymmetric centre when p=1 only.

The compounds of the formula (I) wherein p has the value 0 or 2 contain at least one asymmetric centre and will therefore exist as a pair of enantiomers or as diastereomeric pairs of enantiomers. The compounds of the formula (I) wherein p has the value 1 contain at least two asymmetric centres and will therefore exist as at least two diastereomeric pairs of enantiomers. Such enantiomers or diastereomeric pairs of enantiomers may be separated by physical methods, e.g. by fractional crystallisation, chromatography or H.P.L.C. of the stereoisomeric mixture of the parent compound or of a suitable salt or derivative thereof. Most preferably, the individual enantiomers of the compounds of the formula (I) containing one asymmetric centre, wherein p has the value 0 or 2, are prepared from optically pure intermediates. The invention includes both the individual stereoisomers of the compounds of the formula (I) together with mixtures thereof.

The preferred compounds of the formula (I) provided by the invention have the (2S)-configuration, i.e.

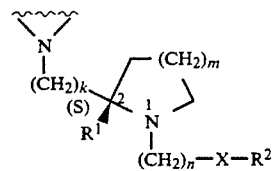

A particularly preferred individual compound is (S)-5,11-dihydro-5-[1-(4-methoxyphenethyl)-2-pyrrolidinylmethyl]dibenzo[b,e][1,4]thiazepine or a pharmaceutically acceptable salt thereof.

The pharmaceutically acceptable salts of the compounds of the formula (I) include acid addition salts formed from acids which form non-toxic salts such as the hydrochloride, hydrobromide, hydroiodide, sulphate, bisulphate, phosphate, hydrogen phosphate, acetate, maleate, fumarate, lactate, tartrate, citrate, gluconate, mandelate, benzoate, salicylate, methanesulphonate, benzenesulphonate and para-toluenesulphonate salts.

Preferably, the acid addition salt is a hydrochloride, maleate, mandelate, salicylate or methanesulphonate.

More preferably, the acid addition salt is a maleate or salicylate.

Most preferably, the acid addition salt is a maleate.

DETAILED DESCRIPTION OF THE INVENTION

The compounds of the formula (I) provided by the invention may be prepared by the following methods:

1) The compounds of the formula (I) wherein k is 1 and m, n, p, X, $R^1$ and $R^2$ are as previously defined for a compound of the formula (I) may be prepared according to Scheme 1:

Scheme 1

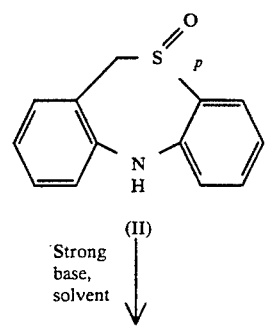

(II)

Strong base, solvent

-continued

Scheme 1

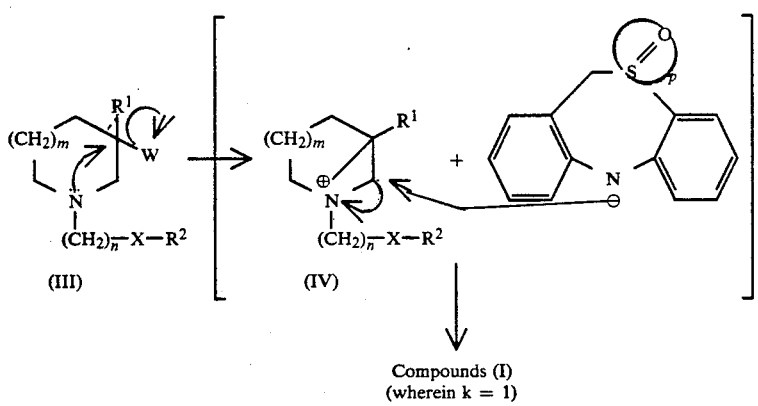

Compounds (I)
(wherein k = 1)

wherein m, n, p, X, R¹ and R² are as previously defined for a compound of the formula (I) and W is a suitable leaving group, e.g. halo (preferably chloro).

In a typical procedure, a compound of the formula (II) is deprotonated by the addition of approximately one equivalent of a suitable strong base, e.g. sodium or potassium hydride, and the anion generated is reacted in situ with a compound of the formula (III) in a suitable organic solvent, e.g. 1,2-dimethoxyethane, at from room temperature to, and preferably at, the reflux temperature thereof.

The reaction proceeds by nucleophilic attack of the anion formed from (II) with an aziridinium ion (IV) generated from (III) in situ (see review article-M. Miocque and J. P. Duclos, Chimie Therapeutique, 1969 (5), 363-380).

The purified product of the formula (I) is isolated from the mixture of by-products also obtained by conventional extraction and chromatographic techniques.

2) All compounds of the formula (I) wherein k, m, n, p, X, R¹ and R² are as previously defined for a compound of the formula (I) may be prepared according to Scheme 2:

Scheme 2

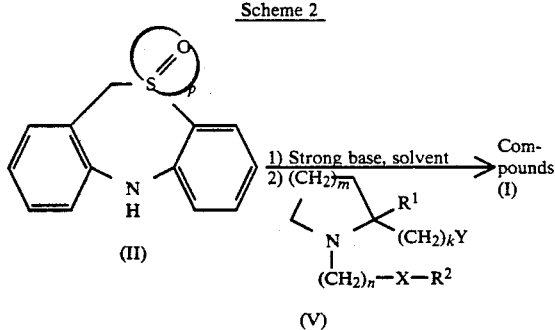

wherein k, m, n, p, X, R¹ and R² are as previously defined for a compound of the formula (I) and Y is a suitable leaving group, e.g. halo (preferably chloro or bromo), methanesulphonyloxy, trifluoromethanesulphonyloxy or p-toluenesulphonyloxy.

Preferably, k is 2 or 3 in this method. When k is 1 the reaction will proceed via the intermediacy of an aziridinium ion (IV) as in method (1).

In a typical procedure, a compound of the formula (II) is deprotonated by the addition of approximately one equivalent of a suitable strong base, e.g. sodium or potassium hydride, and reacted in situ with a compound of the formula (V) in a suitable organic solvent, e.g. 1,2-dimethoxyethane, at from room temperature to, and preferably at, the reflux temperature thereof. The product of the formula (I) is isolated and purified by conventional techniques.

3) All compounds of the formula (I) wherein k, m, n, p, X, R¹ and R² are as previously defined for a compound of the formula (I) may be prepared according to Scheme 3:

Scheme 3

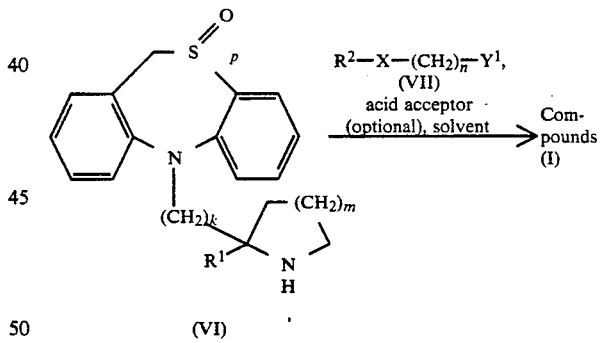

wherein k, m, n, p, X, R¹ and R² are as previously defined for a compound of the formula (I) and Y¹ is a suitable leaving group, e.g. halo (preferably chloro, bromo or iodo), methanesulphonyloxy, trifluoromethanesulphonyloxy or p-toluenesulphonyloxy.

In a typical procedure, a compound of the formula (VI) is reacted with a compound of the formula (VII) in the presence of a suitable acid acceptor, e.g. sodium or potassium carbonate, and, where Y¹ is chloro or bromo, optionally in the presence of sodium or potassium iodide to accelerate the rate of reaction. The reaction is typically carried out in a suitable organic solvent, e.g. acetonitrile, at from room temperature to, and preferably at, the reflux temperature thereof. The product of the formula (I) is isolated and purified by conventional techniques.

4) The compounds of the formula:

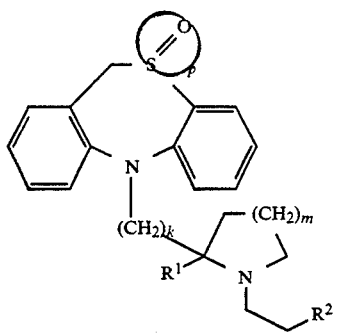

(IA)

wherein k, m, p and R¹ are as previously defined for a compound of the formula (I) and R² is a 2-or 4-pyridinyl, pyridazinyl, 2- or 4-pyrimidinyl or pyrazinyl group, said group being optionally substituted by up to 2 substituents each independently selected from $C_1$–$C_4$ alkyl and $C_1$–$C_4$ alkoxy, may be conveniently prepared by a "Michael-type" addition reaction according to Scheme 4:

Scheme 4

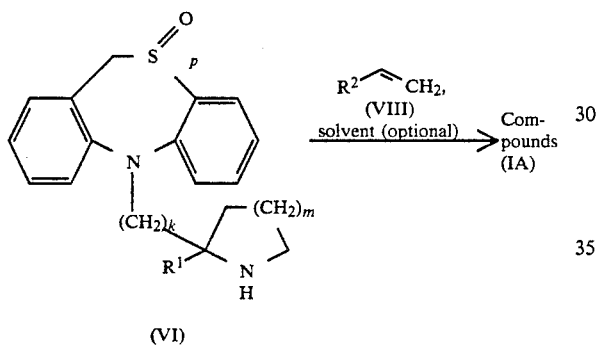

wherein k, m, p, R¹ and R² are as defined for this method.

In a preferred procedure, a compound of the formula (VI) is heated with an excess of a vinylheterocycle (VIII) at from 40° to 140° C., preferably at about 120° C., in the absence of an additional organic co-solvent. The reaction may also be carried out using at least one equivalent of (VIII) in a suitable organic solvent, e.g. 1,4-dioxane, at from 40° C. to the reflux temperature thereof. Optionally, the reaction rate may be accelerated by the addition of a suitable acidic, e.g. acetic acid, or basic catalyst, e.g. benzyltrimethylammonium hydroxide. The product of the formula (I) is isolated and purified by conventional techniques.

5) The compounds of the formula (I) wherein p is 1 or 2 and k, m, n, X, R¹ and R² are as previously defined for a compound of the formula (I) may be prepared by oxidation of a suitable acid addition salt (e.g. a hydrochloride salt) of a compound of the formula (I) wherein p is 0 or 1, as appropriate, and k, m, n, X, R¹ and R² are as previously defined for a compound of the formula (I). The reaction is typically carried out using one or two equivalents, as appropriate, of a suitable oxidising agent, e.g. meta-chloroperbenzoic acid, in a suitable organic solvent, e.g. dichloromethane or chloroform, at from 0° C. to the reflux temperature thereof, and preferably at room temperature.

Alternatively a compound of the formula (I) wherein p is 2 may be prepared by oxidising a suitable acid addition salt (e.g. a hydrochloride salt) of a compound of the formula (I) wherein p is 0 or 1 with an excess of hydrogen peroxide in a $C_1$–$C_4$ alkanoic acid, e.g. formic or acetic acid, at from room temperature to the reflux temperature thereof, and preferably at from 80° to 100° C.

The product of the formula (I) is isolated and purified by conventional techniques.

6) The compounds of the formula (I) wherein p is 0 and k, m, n, X, R¹ and R² are as previously defined for a compound of the formula (I) may be prepared by reduction of a compound of the formula (I) wherein p is 1 or 2 and k, m, n, X, R¹ and R² are as previously defined for a compound of the formula (I).

In a typical procedure a compound of the formula (I) wherein p is 1 or 2 is reacted with a suitable reducing agent, e.g. lithium aluminium hydride, in a suitable organic solvent, e.g. tetrahydrofuran, at from 0° C. to the reflux temperature of the solvent. Usually the reducing agent is added at from 0° C. to room temperature followed by a short period of stirring at from room temperature to the reflux temperature to accelerate the rate of reaction. The product is isolated and purified by conventional techniques.

7) All compounds of the formula (I) wherein k, m, n, p, X, R¹ and R² are as previously defined for a compound of the formula (I) may be prepared by reduction of a compound of the formula:

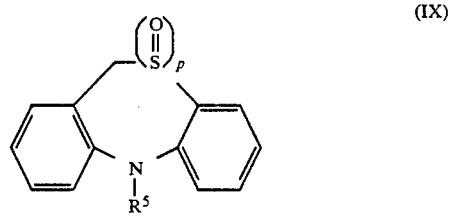

(IX)

wherein p is 0, 1 or 2 and R⁵ is

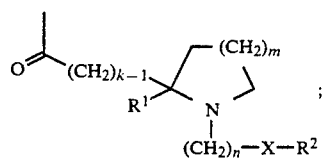

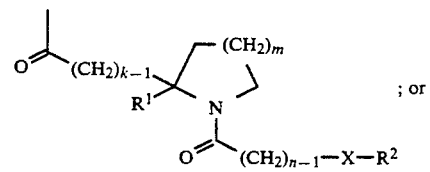
; or

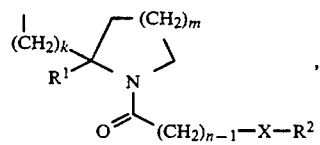

wherein k, m, n, X, R¹ and R² are as previously defined for a compound of the formula (I). Preferably p is 0 in this method.

In a typical procedure a compound of the formula (IX) is reacted with a suitable reducing agent, e.g. borane, in a suitable organic solvent, e.g. tetrahydrofuran or diethyl ether, at from 0° C. to the reflux temperature of the solvent. The reducing agent is usually added at from 0° C. to room temperature and then the rate of reaction accelerated by heating at the reflux temperature for several hours. The product of the formula (I) is isolated and purified by conventional techniques.

In a preferred procedure borane is used as the reducing agent and it is generated in situ using sodium borohydride and boron trifluoride etherate.

8) All compounds of the formula (I) wherein k, m, n, p, X, $R^1$ and $R^2$ are as previously defined for a compound of the formula (I) may be prepared by a Jourdan-Ullmann-Goldberg synthesis using as the starting material a compound of the formula:

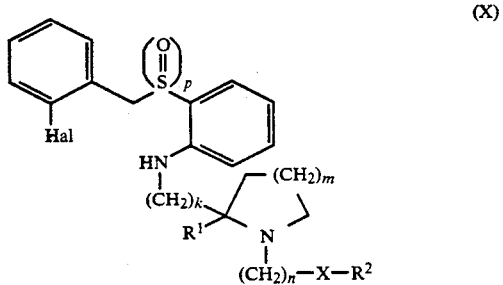

(X)

wherein "Hal" is halo, preferably chloro, bromo or iodo and most preferably bromo, and k, m, n, p, X, $R^1$ and $R^2$ are as previously defined for a compound of the formula (I).

In a typical procedure a compound of the formula (X) is reacted with a suitable transition metal, e.g. copper, or an oxide thereof, in a suitable organic solvent, e.g. pyridine, and optionally in the presence of a suitable inorganic acid acceptor, e.g. potassium carbonate. The reaction may be carried out at from room temperature to the reflux temperature of the solvent, preferably at from 40° C. to the reflux temperature, and most preferably at the reflux temperature. The transition metal used in this process is preferably employed as the powdered metal. The product of the new formula (I) is isolated and purified by conventional techniques.

9) Some of the compounds of the formula (I) wherein $R^2$ is a substituted phenyl group may be prepared from other compounds of the formula (I) by "functional group interconversion", as follows:

a) A hydroxy substituent may be converted to $C_1$-$C_4$ alkoxy by alkylation in the presence of a suitable base. In a typical procedure the phenol is first reacted with a suitable strong base, e.g. sodium hydride, and then treated with a suitable alkylating agent, e.g. a $C_1$-$C_4$ alkyl halide, preferably a bromide or iodide. The reaction usually proceeds at about room temperature in a suitable organic solvent, e.g. tetrahydrofuran or N,N-dimethylformamide, although elevated temperatures may be used.

b) A $C_1$-$C_4$ alkoxy substituent, preferably methoxy, may be converted to hydroxy by treatment with either hydrogen bromide or a $C_1$-$C_4$ alkanethiolate. The reaction with hydrogen bromide may be carried out in acetic acid, or by using aqueous hydrobromic acid. The reaction may be carried out at from room temperature to the reflux temperature of the mixture in both cases. The reaction with a $C_1$-$C_4$ alkanethiolate, such as sodium ethanethiolate or butanethiolate, is typically carried out in a suitable organic solvent, e.g. N,N-dimethylformamide, at from room temperature to the reflux temperature of the solvent. The $C_1$-$C_4$ alkanethiolate reagent may also be generated in situ from the corresponding thiol and a suitable strong base, e.g. sodium hydride.

c) A halo substituent may be converted to —N($C_1$-$C_4$ alkyl)$_2$ by treatment with the appropriate dialkylamine of the formula ($C_1$-$C_4$ alkyl)$_2$NH, optionally in the presence of a suitable inorganic acid acceptor, e.g. sodium carbonate. The reaction is typically carried out in a suitable solvent, e.g. ethanol, at from room temperature to, and preferably at, the reflux temperature. The reaction is most preferably carried out in a "bomb" or sealed tube.

The starting materials of the formula (II) wherein p is 0 or 1 are known compounds and may be prepared in accordance with literature procedures, e.g. for p=0, see U.S. Pat. No. 3,188,322 (Chem. Abs., 63, 8384h (1965)) and I. Ueda and S. Umio, Bull. Chem. Soc. Japan, 48(8), 2323 (1975); and for p=1, see J. Med. Chem., 13, 713 (1970).

The starting materials of the formula (II) wherein p is 2 may be prepared by a similar procedure to that used for the 7-chloro analogue (Table III, Example 38) in J. Med. Chem., 13, 713 (1970).

The intermediates of the formulae (III) and (V) may be prepared as shown in Scheme 5:

Scheme 5

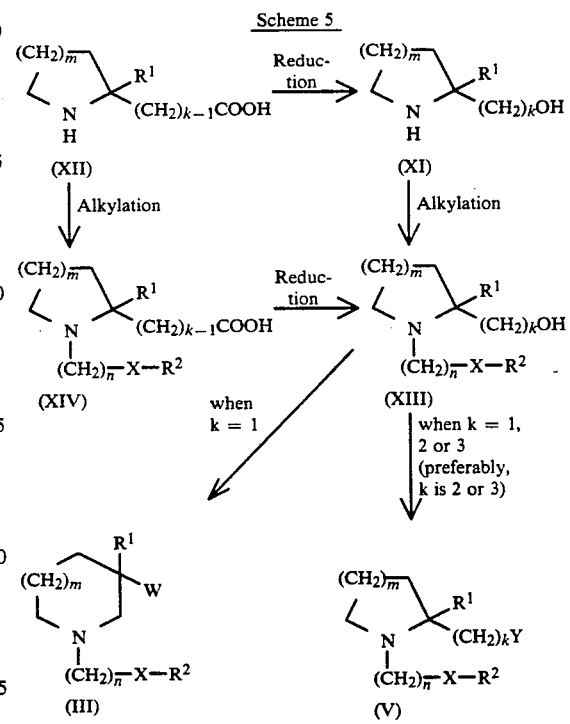

wherein k, m, n, X, $R^1$ and $R^2$ are as previously defined for a compound of the formula (I), W is a suitable leaving group, e.g. halo (preferably chloro), and Y is a suitable leaving group, e.g. halo (preferably chloro or bromo), methanesulphonyloxy, trifluoromethanesulphonyloxy or p-toluenesulphonyloxy.

Accordingly, a compound of the formula (XI) or (XII) may be alkylated with a compound (VII) of the formula $R^2$—X—$(CH_2)_n$—$Y^1$ wherein $R^2$, X and n are as previously defined for a compound of the formula (I) and $Y^1$ is a suitable leaving group, e.g. halo (preferably chloro, bromo or iodo), methanesulphonyloxy, trifluoromethanesulphonyloxy or p-toluenesulphonyloxy, to provide a compound of the formula (XIII) or (XIV), respectively. The reaction is typically carried out in the presence of a suitable acid acceptor, e.g. sodium carbonate, in a suitable organic solvent, e.g. acetonitrile or ethanol, at from room temperature to, and preferably at, the reflux temperature thereof. Where Y is chloro or bromo, sodium or potassium iodide may also be added to accelerate the rate of reaction.

Alternatively, a compound of the formula (XIII) or (XIV) wherein k, m and $R^1$ are as previously defined for a compound of the formula (I), n is 2, X is a direct link and $R^2$ is a 2- or 4-pyridinyl, pyridazinyl, 2- or 4-pyrimidinyl or pyrazinyl group, said group being optionally substituted by up to 2 substituents each independently selected from $C_1$-$C_4$ alkyl and $C_1$-$C_4$ alkoxy, may be conveniently prepared by heating a compound of the formula (XI) or (XII), respectively, with an appropriate vinylheterocycle (VIII) of the formula $R^2CH=CH_2$ (wherein $R^2$ is as previously defined in this method), optionally in a suitable organic solvent, e.g. 1,4-dioxane, at from 40° to 140° C. or at the reflux temperature of said organic solvent. Optionally, the reaction rate may be accelerated by the addition of a suitable acidic e.g. acetic acid, or basic catalyst, e.g. benzyltrimethylammonium hydroxide.

The reduction of a compound of the formula (XII) or (XIV) to a compound of the formula (XI) or (XIII), respectively, may be carried out using a suitable reducing agent, e.g. lithium aluminium hydride. In a typical procedure, the reduction is carried out in a suitable organic solvent, e.g. tetrahydrofuran, at from 0° C. to the reflux temperature thereof. Optionally, compound (XII) may be used in the form of a suitable acid addition salt, e.g. a hydrochloride or hydrobromide, in this process.

The compounds of the formula (III) wherein W is halo (preferably chloro) may be prepared from a compound of the formula (XIII) (wherein k=1) by treatment with either (i) a suitable halogenating agent, e.g. thionyl chloride or bromide, preferably in the presence of a suitable organic solvent, e.g. dichloromethane or chloroform, at from room temperature to, and preferably at, the reflux temperature thereof; or (ii) a $C_1$-$C_4$ alkanesulphonyl chloride or bromide, e.g. methanesulphonyl chloride or bromide, in the presence of a suitable acid acceptor, e.g. triethylamine, in a suitable organic solvent, e.g. dichloromethane, at from room temperature to the reflux tempertaure thereof, and preferably at room temperature.

The compound of the formula (V) may be prepared from the compound (XIII) by treatment with either (i) a suitable halogenating agent, e.g. thionyl chloride or bromide, preferably in the presence of a suitable organic solvent, e.g. dichloromethane or chloroform, at from room temperature to, and preferably at, the reflux temperature thereof; or (ii) a $C_1$-$C_4$ alkanesulphonyl chloride or bromide (e.g. methanesulphonyl chloride), a $C_1$-$C_4$ alkanesulphonic anhydridride (e.g. methanesulphonic anhydride), trifluoromethanesulphonic anhydride or p-toluenesulphonyl chloride, in the presence of a suitable acid acceptor, e.g. triethylamine, and in a suitable organic solvent, e.g. dichloromethane, at from 0° C. to the reflux temperature thereof.

The skilled man will appreciated that the attempted conversion of (XIII) to (V) when k is 1 under certain conditions may lead to the isolation of (III) as the reaction product as a result of rearrangement of (V) in situ via an aziridinium ion (IV) (as indicated above). Consequently the reaction path followed may be difficult to predict and may vary according to the individual compound (XIII) used and the conditions employed. However, either product (III) or (V) obtained may be used as the starting material for the preparation of the appropriate compound of the formula (I) (see Methods (1) and (2)).

The optically pure or racemic starting materials of the formula (XI) or (XII), the alkylating agents (VII) of the formula $R^2$—X—$(CH_2)_n$—$Y^1$ and the vinylheterocycles (VIII) of the formula $R^2CH=CH_2$ are either known compounds which may also be commercially available, or are preparable by conventional procedures in accordance with literature precedents such as those illustrated in the following Preparations section.

The intermediates of the formula (VI) may be prepared as shown in Scheme 6:

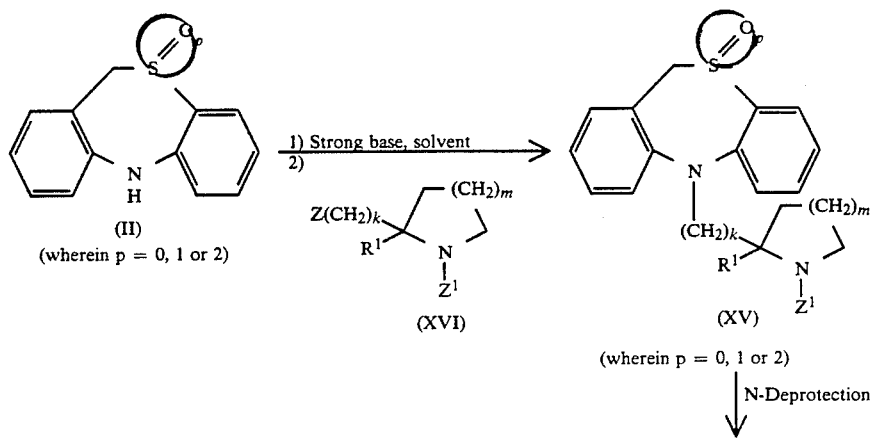

Scheme 6

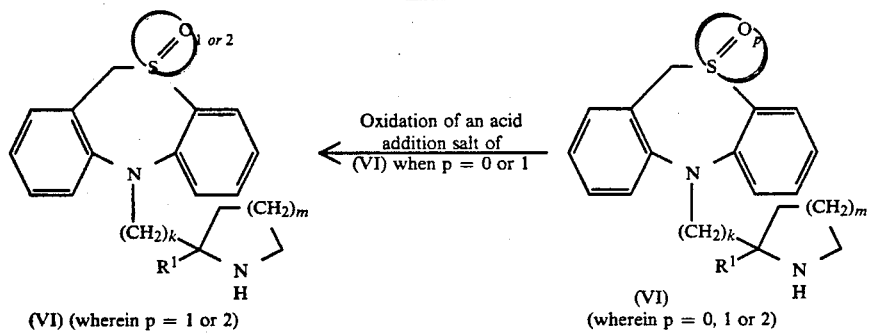

(VI) (wherein p = 1 or 2)      (VI) (wherein p = 0, 1 or 2)

wherein k, m, p and $R^1$ are as previously defined for a compound of the formula (I), Z is a suitable leaving group, e.g. p-toluenesulphonyloxy, and $Z^1$ is a suitable protecting group, e.g. p-toluenesulphonyl.

In a typical procedure, a compound of the formula (II) is deprotonated by the addition of approximately one equivalent of a suitable strong base in a suitable organic solvent. Preferred base/solvent combinations are lithium diisopropylamide/1,2-dimethoxyethane or sodium hydride/N,N-dimethylformamide. The anion generated is then reacted in situ with a compound of the formula (XVI) to provide compound (XV).

N-Deprotection of a compound of the formula (XV) wherein p=0 and $Z^1$ is p-toluenesulphonyl is achieved using, e.g. sodium bis(2-methoxyethoxy)aluminium hydride ("Red-Al"—Registered Trade Mark) in toluene or sodium/naphthalene/1,2-dimethoxyethane to provide a compound of the formula (VI).

Preferably, a compound of the formula (VI) wherein p=1 or 2 is prepared by oxidation of an acid addition salt of a compound of the formula (VI) wherein p is 0 as described below.

A compound of the formula (VI) wherein p is 0 or 1 can be optionally oxidised in the form of a suitable acid addition salt (e.g. a hydrochloride) to provide the compound of the formula (VI) wherein p is 1 or 2, as appropriate. The reaction is typically carried out using one or two equivalents, as appropriate, of a suitable oxidising agent, e.g. meta-chloroperbenzoic acid, in a suitable organic solvent, e.g. chloroform, and at from 0° C. to the reflux temperature thereof, and preferably at room temperature. Alternatively a compound of the formula (VI) wherein p is 2 may be prepared by oxidising a suitable acid addition salt (e.g. a hydrochloride salt) of a compound of the formula (VI) wherein p is 0 or 1 with an excess of hydrogen peroxide in a $C_1$-$C_4$ alkonoic acid, e.g. formic or acetic acid, at from room temperature to the reflux temperature thereof.

The choice of a suitable leaving group (Z) and protecting group ($Z^1$) combination in the compounds of the formula (XVI), as well as suitable conditions for the N-deprotection of a compound of the formula (XV) will be well known to a man skilled in the art.

Intermediates of the formula (XVI) are either known compounds (e.g. see P. Karrer and K. Ehrhardt, Helv. Chim. Acta, 34, 2202 (1951)) or are prepared by conventional procedures in accordance with literature precedents, e.g. using compounds of the formula (XI) as starting materials.

The intermediates of the formula (IX) may be prepared by conventional condensation or acylation methods, for example, (i) by condensation of a compound of the formula (II), wherein p is 0, 1 or 2, with a compound of the formula (XIV) or

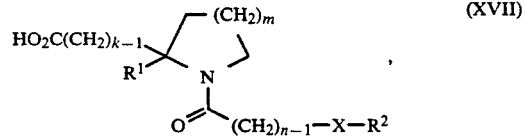

as appropriate, wherein k, m, n, X, $R^1$ and $R^2$ are as previously defined for a compound of the formula (I);

(ii) by condensation of a compound of the formula (VI), wherein k, m, p and $R^1$ are as previously defined for a compound of the formula (I), with a compound (XVIII) of the formula $R^2$—X—$(CH_2)_{n-1}CO_2H$ wherein n, X and $R^2$ are as previously defined for a compound of the formula (I); or (iii) by acylation of a compound of the formula (II) or (VI), as appropriate, with a suitable acyl halide (preferably chloride) derivative of (XIV), (XVII) or (XVIII), as appropriate, wherein k, m, n, p, X, $R^1$ and $R^2$ are as previously defined for a compound of the formula (I), typically in the presence of a suitable acid acceptor such as pyridine, triethylamine or sodium or potassium carbonate or bicarbonate, and in a suitable organic solvent, e.g. dichloromethane. In the condensation methods (i) and (ii) above, conventional peptide coupling techniques may be employed, e.g. using 1,3-dicyclohexylcarbodiimide or 1,1'-carbonyldiimidazole as activating agents for the carboxyl group.

The compounds of the formula (XVII) may be prepared either by condensation of a compound of the formula (XII), wherein m, k and $R^1$ are as previously defined for a compound of the formula (I), with a compound of the formula (XVIII), wherein n, X and $R^2$ are as previously defined for a compound of the formula (I), or by acylation of a compound of the formula (XII), or of a base salt (e.g. sodium salt) thereof, with a suitable acyl halide derivative of a compound of the formula (XVIII), using similar procedures to those previously described for the preparation of compounds of the formula (IX), and as illustrated in the following Preparations section.

The starting materials of the formula (XVIII), and the corresponding acyl halide derivatives thereof, are either known compounds which may also be commercially available, or are prepared by conventional methods in accordance with literature precedents.

The intermediates of the formula (X) are most conveniently prepared firstly by condensation or acylation of a compound of the formula:

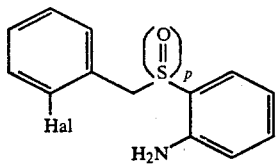
(XIX)

wherein p and "Hal" are as previously defined for a compound of the formula (X), with a compound of the formula (XIV) or (XVII), or a suitable acyl halide derivative thereof, as appropriate, wherein k, m, n, X, $R^1$ and $R^2$ are as previously defined for a compound of the formula (I), by conventional condensation or acylation techniques such as those previously described for the preparation of compounds of the formula (IX), to provide an intermediate amide of the formula:

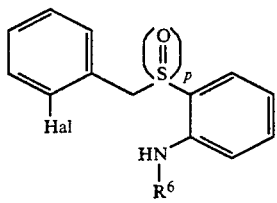
(XX)

wherein "Hal" is halo, preferably chloro, bromo or iodo and most preferably bromo, p is 0, 1 or 2 and $R^6$ is

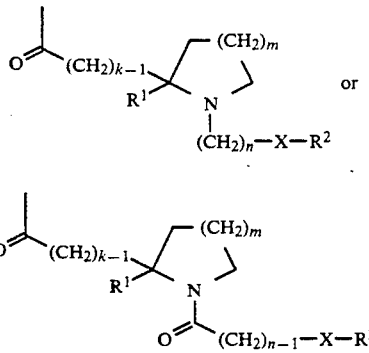

respectively, wherein k, m, n, X, $R^1$ and $R^2$ are as previously defined for a compound of the formula (I), followed by reduction of the compound of the formula (XX) with a suitable reducing agent, e.g. borane, using a similar method to that previously described in method (7) for the preparation of compounds of the formula (I). Preferably p is 0 in this method.

The starting materials of the formula (XIX) may be known compounds (e.g. see Bull. Chem. Soc. Japan, 48, 2323 (1975)) or are prepared by conventional techniques in accordance with literature precedents.

All of the above reactions are conventional and appropriate reagents and reaction conditions for their performance and procedures for isolating the desired products will be well known to those skilled in the art in accordance with literature precedents and by reference to the Examples and Preparations hereto.

Pharmaceutically acceptable acid addition salts are readily prepared by mixing equimolar amounts of the free base and the desired acid together in a suitable solvent. The acid addition salt generally precipitates from solution and is collected by filtration, or is recovered by evaporation of the solvent. The salt obtained may be recrystallised if further purification is desired.

ASSESSMENT OF IN VITRO SPASMOLYTIC ACTIVITY

The activity of the compounds of the invention may be shown according to the following methods.

Intestinal spasmolytic activity is assessed using isolated pieces of guinea pig ileum in vitro. Tissues are equilibrated in normal Krebs solution at 37° C. and gassed with 95% oxygen and 5% carbon dioxide. One end of the tissue is fixed and the opposite end attached to a Washington isotonic transducer. Contractions are induced by electrical field stimulation (0.1 Hz, 0.5 msec at supramaximal voltage) and the magnitude of the response assessed. Tissues are treated at 15 minute intervals with increasing concentrations of test compound with a washout between each concentration. The concentration of compound required to reduce the response by 50% ($ED_{50}$) is determined. Alternatively tissues are contracted with a submaximal concentration of either acetylcholine, histamine or bradykinin using a 3 minute contact period and the magnitude of the response noted. The bath is drained and replaced with fresh Krebs solution and, after 20 minutes, the test is repeated with the particular test compound present in the Krebs solution. The concentration of compound required to reduce the response by 50% ($ED_{50}$) is determined. Finally, tissues may be incubated in modified Krebs solution containing 45 mM $K^+$ and zero $Ca^{2+}$ concentration. Tissues are contracted by the addition of 2 mM $Ca^{2+}$ and the magnitude of the resulting contraction recorded. The bath is drained and replaced with fresh modified Krebs solution and, after 20 minutes, the test is repeated with the particular test compound present in the Krebs solution. The concentration of compound required to inhibit the response by 50% ($ED_{50}$) is determined.

Spasmolytic activity on vascular tissue is shown by the ability of compounds to inhibit contractile responses of vascular tissues in vitro which is the consequence of calcium influx caused by high extracellular concentrations of potassium ions. The test is performed by mounting spirally cut strips of rat aorta with one end fixed and the other attached to a force transducer. The tissue is immersed in Krebs solution containing 2.5 mM $Ca^{2+}$. Potassium chloride is added to the bath to give a final $K^+$ concentration of 45 mM. The change in tension caused by the resulting contraction of the tissue is noted. The bath is drained and replaced with fresh Krebs solution and, after 45 minutes, the test is repeated with the particular compound under test in the Krebs solution. The concentration of compound required to reduce the response by 50% ($ED_{50}$) is recorded.

A compound which is gut selective inhibits the spasmogenic response of the guinea pig ileum at a lower $ED_{50}$ concentration than that measured for the rat aorta.

ASSESSMENT OF IN VIVO SPASMOLYTIC ACTIVITY

The spasmolytic activity in vivo of the compounds of the invention is assessed by determining the ability of the test compound to inhibit cholecystokinin stimulated intestinal motility in anaesthetised dogs in comparison with changes in heart rate, blood pressure, cardiac output and total peripheral resistance. Oral activity is assessed in normal conscious dogs instrumented to record small and large bowel motility.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of motility disorders of the gut, oral dosages of the compounds will generally be in the range of from 1 to 1000 mg.

Thus, the invention further provides a pharmaceutical composition comprising a compound of the formula (I), or a pharmaceutically acceptable salt thereof, together with a pharmaceutically acceptable diluent or carrier.

The invention yet further provides a compound of the formula (I), or a pharmaceutically acceptable salt thereof, for use as a medicament.

The invention also provides the use of a compound of the formula (I), or of a pharmaceutically acceptable salt thereof, for the manufacture of a medicament for the treatment of motility disorders, particularly those of the gut such as irritable bowel syndrome.

The invention further provides a method of treating an animal (including a human being) to cure or prevent a motility disorder, particularly of the gut such as irritable bowel syndrome, which comprises treating said animal with an effective amount of a compound of the formula (I), or with, as appropriate, a pharmaceutically acceptable salt or composition thereof.

The invention also includes any novel intermediates disclosed herein, such as those of the formulae (VI), (IX) and (X).

The following Examples illustrate the preparation of the compounds of the invention:

EXAMPLE 1

(S)-5,11-Dihydro-5-[1-(4-methoxyphenethyl)-2-pyrrolidinylmethyl]dibenzo[b,e][1,4]thiazepine

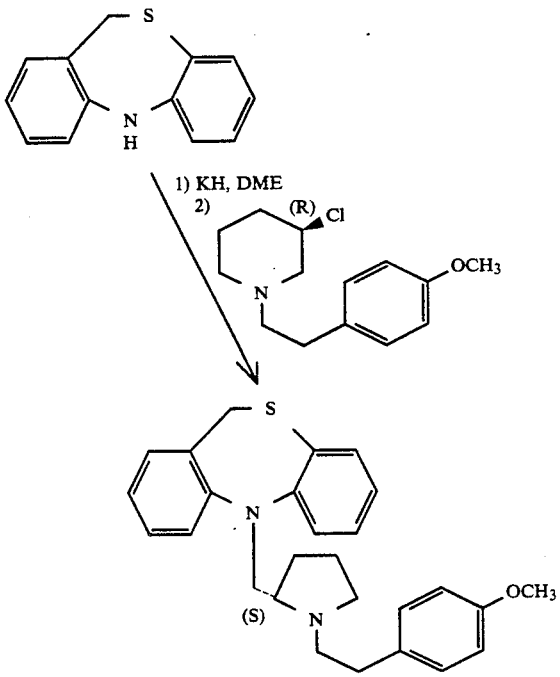

Potassium hydride (35% dispersion in oil, 229 mg) was added to a solution of 5,11-dihydrodibenzo[b,e][1,4]thiazepine (see U.S. Pat. No. 3,188,322 [Chem. Abs., 63, 8384h (1965)] and I. Udea and S. Umio, Bull. Chem. Soc. Japan, 48(8), 2323 (1975)) (425 mg) in DME (1,2-dimethoxyethane) (20 ml) and the mixture stirred at room temperature for 30 minutes, treated with a solution of (R)-3-chloro-1-(4-methoxyphenethyl)piperidine (see Preparation 1) (507 mg) in DME (5 ml) and heated under reflux for 18 hours. The mixture was cooled to room temperature, quenched with water and extracted with ethyl acetate. The organic layer was washed with water, dried over sodium sulphate and evaporated under reduced pressure. The residue was purified by chromatography on silica gel, performing a gradient elution using initially dichloromethane as eluant and changing to dichloromethane/saturated methanolic ammonia (98:2). The appropriate fractions were combined and evaporated under reduced pressure to give the title compound as a colourless oil, (100 mg, 12%), $[\alpha]_{589}^{25} -60.9°$ (c=0.57 in ethanol).

$^1$H-NMR (300 MHz, CDCl$_3$) δ=6.8–7.4 (m, 12H), 4.65 (broad, 1H), 4.15 (dd, 2H, J=8 Hz and 2 Hz), 3.82 (s, 3H), 3.12 (m, 2H), 3.0 (m, 1H), 2.78 (m, 2H), 2.55 (m, 2H), 2.25 (q, 1H, J=8 Hz), 1.7–2.0 (m, 4H) ppm.

Analysis %: Found: C,75.0; H,6.9; N,6.0. C$_{27}$H$_{30}$N$_2$OS requires: C,75.3; H,7.0; N,6.5.

EXAMPLES 2 TO 4

The following tabulated Examples of the general formula:

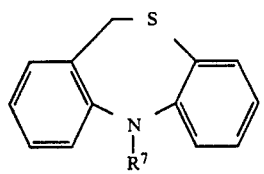

were obtained as colourless oils by similar methods to that described for Example 1 using 5,11-dihydrodibenzo[b,e][1,4]thiazepine and the appropriate chloro compound as starting materials.

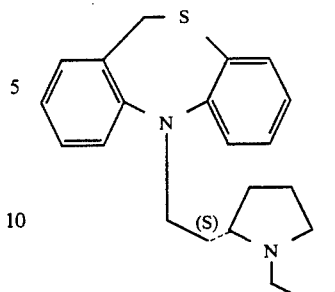

| Example No. | Product stereochemistry | "Chloro Compound" | $R^7$ | Analysis % |
|---|---|---|---|---|
| 2 | R | (see Preparation 2) | | Found: C, 75.1; H, 6.9; N, 6.1; $C_{27}H_{30}N_2OS$ requires: C, 75.3; H, 7.0; N, 6.5. |
| 3 | S | (see Preparation 3) | | Found: C, 75.7; H, 7.1; N, 6.1; $C_{28}H_{32}N_2OS$ requires: C, 75.6; H, 7.3; N, 6.3. |
| 4 | S | (see Preparation 5) | | Found: C, 75.3; H, 7.3; N, 6.2; $C_{28}H_{32}N_2OS$ requires: C, 75.6; H, 7.3; N, 6.3. |

EXAMPLE 5

(S)-5,11-Dihydro-5-[2-(1-[4-methoxyphenethyl]-2-pyrrolidinyl)ethyl]dibenzo[b,e][1,4]thiazepine

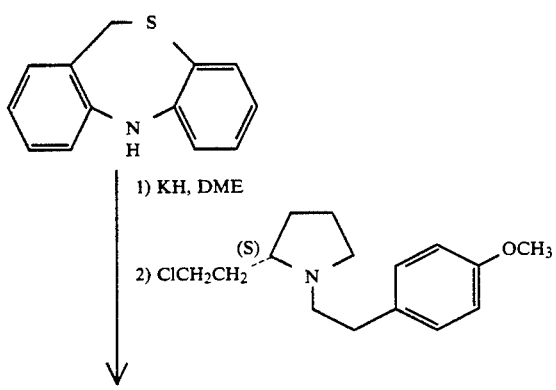

Potassium hydride (35% dispersion in oil, 110 mg) was added to a solution of 5,11-dihydrodibenzo[b,e][1,4]thiazepine (see Example 1) (570 mg) in DME (8 ml) and the mixture stirred at room temperature for 30 minutes, treated with a solution of (S)-2-(2-chloroethyl)-1-(4-methoxyphenethyl)pyrrolidine (480 mg) (prepared from the corresponding hydrochloride salt prepared in Preparation 4 by stirring a solution of the salt in dichloromethane with a slight excess of 10% aqueous sodium carbonate solution, separating the layers, drying the organic layer over sodium sulphate, and evaporating under reduced pressure to provide the desired free base) in DME (4 ml) and heated under reflux for two hours. The mixture was cooled to room temperature, quenched with water and extracted with ethyl acetate. The organic layer was washed with water, dried over sodium sulphate and evaporated under reduced pressure. The residue was purified by chromatography on silica gel, performing a gradient elution using initially dichloromethane/hexane (3:1) as eluant, changing to dichloromethane/methanol (97:3). The appropriate fractions were combined and evaporated under reduced pressure to give the title compound as a colourless oil, (460 mg, 58%).

Analysis %: Found: C,75.3; H,7.3; N,6.3. $C_{28}H_{32}N_2OS$ requires: C,75.6; H,7.2; N,6.3.

EXAMPLE 6

(S)-5,11-Dihydro-5-[1-(4-methoxyphenethyl)-2-pyrrolidinylmethyl]dibenzo[b,e][1,4]thiazepine

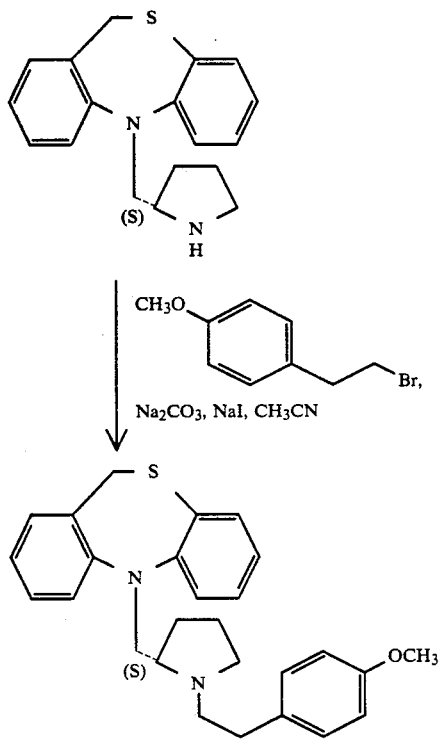

A mixture of (S)-5,11-dihydro-5-(2-pyrrolidinylmethyl)dibenzo[b,e][1,4]thiazepine (see Preparations 13 and 14) (2.8 g), 4-methoxyphenethyl bromide (2.6 g), sodium carbonate (1.30 g) and sodium iodide (50 mg) in acetonitrile (75 ml) was heated under reflux for 16 hours, evaporated under reduced pressure and the residue partitioned between ethyl acetate and water. The organic layer was washed with water, dried over sodium sulphate and evaporated under reduced pressure. The residue was purified by chromatography on silica gel, performing a gradient elution using initially dichloromethane as eluant and changing to dichloromethane/saturated methanolic ammonia (98:2). The appropriate fractions were combined and evaporated under reduced pressure to give the title compound as a colourless oil, (2.5 g, 62%).

$^1$H-NMR (300 MHz, CDCl$_3$) $\delta$=6.8–7.4 (m, 12H), 4.65 (broad, 1H), 4.15 (dd, 2H, J=8 Hz and 2 Hz), 3.82 (s, 3H), 3.12 (m, 2H), 3.0 (m, 1H), 2.78 (m, 2H), 2.55 (m, 2H), 2.25 (q, 1H, J=8 Hz), 1.7–2.0 (m, 4H) ppm.

EXAMPLES 7 to 19

The following tabulated Examples of the general formula:

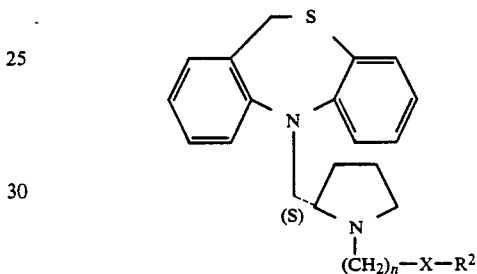

were prepared as oils by similar methods to that described for Example 6 by reacting (S)-5,11-dihydro-5-(2-pyrrolidinylmethyl)dibenzo[b,e][1,4]thiazepine (see Preparations 13 and 14) with a slight excess of the appropriate alkylating agent R$^2$—X—(CH$_2$)$_n$—Y$^1$ in the presence of sodium carbonate and sodium iodide using acetonitrile as the solvent.

| Example No. | R$^2$—X—(CH$_2$)$_n$— | Y$^1$ | Optical Rotation $[\alpha]_{589}^{25}$ | Analysis % |
|---|---|---|---|---|
| 7 | ⌬–CH$_2$CH$_2$— | Br | −67.3° (c = 0.565 in ethanol) | Found: C, 78.1; H, 7.0; N, 7.2; C$_{26}$H$_{28}$N$_2$S requires: C, 78.0; H, 7.0; N, 7.0. |
| 8 | CH$_3$–⌬–CH$_2$CH$_2$— | Br | −61.3° (c = 0.615 in ethanol) | Found: C, 78.6; H, 7.4; N, 6.7; C$_{27}$H$_{30}$N$_2$S requires: C, 78.2; H, 7.3; N, 6.8. |
| 9 | indanyl-CH$_2$CH$_2$— | Br$^{(1)}$ | −57.4° (c = 0.505 in ethanol) | Found: C, 79.4; H, 7.3; N, 6.4; C$_{27}$H$_{32}$N$_2$S requires: C, 79.0; H, 7.3; N, 6.4. |
| 10 | pyrimidinyl-CH$_2$CH$_2$— | —OSO$_2$CH$_3$$^{(2)}$ | — | Found: C, 70.4; H, 6.6; N, 13.1; C$_{24}$H$_{26}$N$_4$S.½H$_2$O requires: C, 70.0; H, 6.6; N, 13.6. |

-continued

| Example No. | $R^2-X-(CH_2)_n-$ | $Y^1$ | Optical Rotation $[\alpha]_{589}^{25}$ | Analysis % |
|---|---|---|---|---|
| 11 | HO—C₆H₄—CH₂CH₂— (4-hydroxyphenyl)ethyl | Br | — | Found: C, 74.2; H, 6.7; N, 6.6; $C_{26}H_{28}N_2OS \cdot \frac{1}{2}H_2O$ requires: C, 74.2; H, 6.8; N, 6.7. |
| 12 | 3-thienyl-CH₂CH₂— | Br | −63.1° (c = 0.585 in ethanol) | Found: C, 71.0; H, 6.4; N, 6.9; $C_{24}H_{26}N_2S_2$ requires: C, 70.9; H, 6.4; N, 6.9. |
| 13 | C₆H₅—OCH₂CH₂CH₂— | Br | −77.1° (c = 0.52 in ethanol) | Found: C, 75.4; H, 7.1; N, 6.5; $C_{27}H_{30}N_2OS$ requires: C, 75.3; H, 7.0; N, 6.5. |
| 14 | 4-CH₃O—C₆H₄—CH₂— | Cl | −42.7° (c = 0.51 in ethanol) | Found: C, 74.7; H, 6.8; N, 6.5; $C_{26}H_{28}N_2OS$ requires: C, 75.0; H, 6.8; N, 6.7. |
| 15 | 3-CH₃—C₆H₄—CH₂CH₂— | Br | −65.9° (c = 0.615 in ethanol) | Found: C, 77.8; H, 7.2; N, 6.7; $C_{27}H_{30}N_2S$ requires: C, 78.2; H, 7.3; N, 6.8. |
| 16 | 3,4-(CH₃O)₂—C₆H₃—CH₂CH₂— | Cl | −36.0° (c = 0.645 in ethanol) | Found: C, 73.2; H, 7.0; N, 5.7; $C_{28}H_{32}N_2O_2S$ requires: C, 73.0; H, 7.0; N, 6.1. |
| 17 | C₆H₅—SCH₂CH₂— | Br | — | Found: C, 72.1; H, 6.5; N, 6.8; $C_{26}H_{28}N_2S_2$ requires: C, 72.2; H, 6.5; N, 6.5. |
| 18 | 4-Cl—C₆H₄—CH₂CH₂— | Br | — | Found: C, 71.4; H, 6.2; N, 6.3; $C_{26}H_{27}ClN_2S$ requires: C, 71.8; H, 6.3; N, 6.4. |
| 19 | 3,4-methylenedioxyphenyl-CH₂CH₂— | Br[3] | — | δ = 6.97–7.35(m, 7H), 6.68–6.88 (m, 4H), 5.97(s, 2H), 4.70(broad s, 1H), 4.03(dd, 2H, J = 10 & 2Hz), 3.13 and 3.23(m, 2H), 2.92–3.04 (m, 1H), 2.64–2.81(m, 2H), 2.45–2.59 (m, 2H), 2.18–2.30(m, 1H), 1.65–2.00 (m, 4H) ppm. |

[1] For preparation of 5-(2-bromoethyl)indane see Preparation 17.
[2] For preparation of 4-(2-[methanesulphonyloxy]ethyl)pyrimidine see Preparation 18.
[3] For preparation of 3,4-methylenedioxyphenethyl bromide see EP-A-0350309.

EXAMPLE 20

(S)-5,11-Dihydro-5-[1-(4-methoxyphenethyl)-2-pyrrolidinylmethyl]dibenzo[b,e][1,4]thiazepine maleate (1:1)

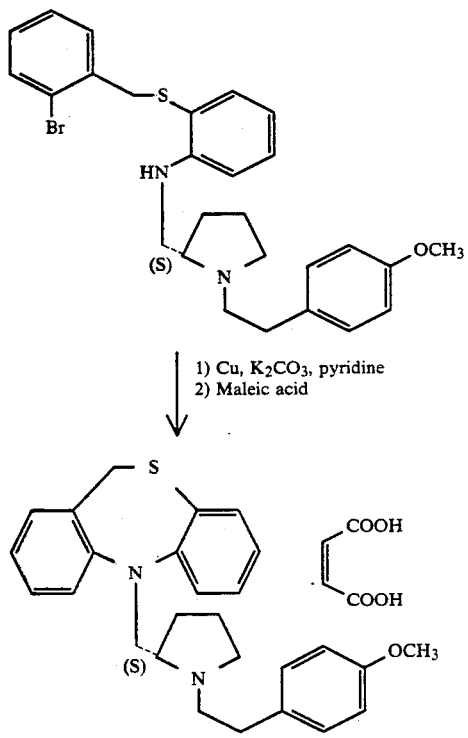

1) Cu, K$_2$CO$_3$, pyridine
2) Maleic acid

A mixture of (2S)-(N-[2(2-bromophenylmethylthio)-phenyl])aminomethyl-1-(4-methoxyphenethyl)pyrrolidine (see Preparation 22) (1580 g), potassium carbonate (854 g) and copper powder (97.6 g) in pyridine (7.9 L) was heated under reflux for 5 days, cooled, filtered and poured into a mixture of concentrated hydrochloric acid (10 L), ice (15 kg) and dichloromethane (2.5 L). The layers were separated and the acidic aqueous layer was extracted three times with dichloromethane. The combined organic extracts were washed with 2M aqueous sodium hydroxide solution followed by water, dried over magnesium sulphate and evaporated under reduced pressure. The residue (1255 g) was dissolved in ethyl acetate (2.5 L) and the solution was treated with a solution of maleic acid (339 g) in ethyl acetate (8.5 L). The resulting precipitate was collected by filtration, washed with ethyl acetate and dried to give the title compound (921 g, 54%) as a colourless solid, m.p. 152.5° C., $[\alpha]_{589}^{25}$ −47.6 (c=1.0 in dichloromethane).

Analysis %: Found: C,68.2; H,6.2; N,5.1; S, 5.8. C$_{27}$H$_{30}$N$_2$OS.C$_4$H$_4$O$_4$ requires: C,68.1; H,6.3; N,5.1; S, 5.9.

EXAMPLE 21

5,11-Dihydro-5-[1-(4-methoxyphenethyl)-2-pyrrolidinylmethyl]dibenzo[b,e][1,4]thiazepine maleate (1:1)

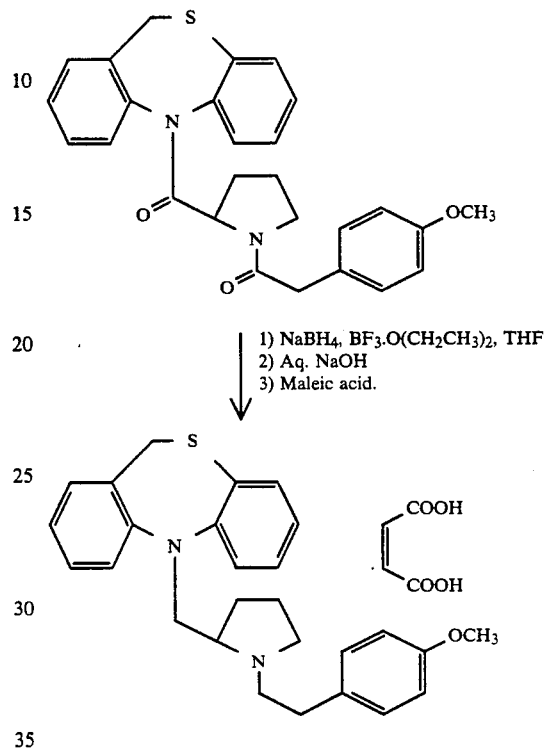

1) NaBH$_4$, BF$_3$.O(CH$_2$CH$_3$)$_2$, THF
2) Aq. NaOH
3) Maleic acid.

Boron trifluoride etherate (23.4 g) was added over 5 minutes to a stirred solution of 5,11-dihydro-5-[1-(4-methoxyphenylacetyl)-2-pyrrolidinylcarbonyl]dibenzo[b,e][1,4]thiazepine (see Preparation 25) (22.9 g) and sodium borohydride (4.22 g) in tetrahydrofuran (120 ml). The mixture was stirred at room temperature for one hour, heated under reflux for two hours, cooled, quenched cautiously with water and evaporated under reduced pressure to reduced volume to remove the tetrahydrofuran. The residue was treated with 4M aqueous sodium hydroxide solution (50 ml) and the mixture was heated under reflux for two hours, allowed to cool to room temperature and extracted with dichloromethane. The organic extracts were dried over magnesium sulphate and evaporated under reduced pressure. The residue (17.6 g) was dissolved in ethyl acetate (40 ml) and the solution was heated to 50° C., treated with a solution of maleic acid (4.74 g) in ethyl acetate (100 ml) and stirred at room temperature for ten minutes. The resulting precipitate was collected by filtration, washed with ethyl acetate and dried to give the desired compound as a colourless solid (19.4 g, 71%), m.p. 174° C.

Analysis %: Found: C, 67.9; H,6.2; N, 5.0. C$_{27}$H$_{30}$N$_2$OS.C$_4$H$_4$O$_4$ requires: C; 68.1; H, 6.3; N,5.1.

EXAMPLE 22

(S)-5,11-Dihydro-5-[1-(4-methoxyphenethyl)-2-pyrrolidinylmethyl]dibenzo[b,e][1,4]thiazepine salicylate (1:1)

A solution of salicylic acid (800 mg) in ether (5 ml) was added to a solution of (S)-5,11-dihydro-5-[1-(4- methoxyphenethyl)-2-pyrrolidinylmethyl]dibenzo[b-,e][1,4]thiazepine (see Examples 1 and 6) (2.50 g) in ether (10 ml) and the mixture was stirred at room temperature for 16 hours. The resulting precipitate was collected, dried and recrystallised from isopropyl acetate to give the title compound as colourless crystals, (2.35 g, 71%), m.p. 150°–151° C., $[\alpha]_{589} -40.6°$ (c=0.695 in ethanol).

Analysis %: Found: C,71.8; H,6.4; N,4.9. $C_{27}H_{30}N_2OS \cdot C_7H_6O_3$ requires: C,71.8; H,6.4; N,4.9.

EXAMPLE 23

(S)-5,11-Dihydro-5-[1-(4-methoxyphenethyl)-2-pyrrolidinylmethyl]dibenzo[b,e][1,4]thiazepine maleate (1:1)

A solution of maleic acid (4.7 g) in ethyl acetate (200 ml) was added to a solution of (S)-5,11-dihydro-5-[1-(4-methoxyphenethyl)-2-pyrrolidinylmethyl]dibenzo[b-,e][1,4]thiazepine (see Examples 1 and 6) (17.3 g) in ethyl acetate (100 ml) and the mixture was stirred at room temperature for 16 hours. The resulting precipitate was collected, dried and recrystallised from ethyl acetate/methanol to give the title compound as colourless crystals, (14.0 g, 64%), m.p. 153°–154° C., $[\alpha]_{589}^{25} -39.7°$ (c=0.755 in ethanol).

Analysis %: Found: C,68.1; H,6.2; N,5.0. $C_{27}H_{30}N_2OS \cdot C_4H_4O_4$ requires: C,68.1; H,6.3; N,5.1.

EXAMPLE 24

(S)-5,11-Dihydro-5-[1-(4-methoxyphenethyl)-2-pyrrolidinylmethyl]dibenzo[b,e][1,4]thiazepine methanesulphonate (1:1)

Methanesulphonic acid (39 mg) was added to a solution of (S)-5,11-dihydro-5-[1-(4-methoxyphenethyl)-2-pyrrolidinylmethyl]dibenzo[b,e][1,4]thiazepine (see Examples 1 and 6) (175 mg) in dichloromethane (5 ml) and the mixture was stirred at room temperature for 16 hours and evaporated under reduced pressure. The residue was crystallised from ethyl acetate/diisopropyl ether to give the title compound as colourless crystals, (150 mg, 31%), m.p. 118°–122° C., $[\alpha]_{589}^{25} -36.9°$ (c=0.59 in ethanol).

Analysis %: Found: C,64.2; H,6.6; N,5.1; $C_{27}H_{30}N_2OS \cdot CH_4O_3S$ requires: C,63.8; H,6.5; N,5.3.

EXAMPLE 25

(S)-5,11-Dihydro-5-[1-(4-methoxyphenethyl)-2-pyrrolidinylmethyl]dibenzo[b,e][1,4]thiazepine (R)-mandelate (1:1)

A solution of (R)-mandelic acid (88 mg) and (S)-5,11-dihydro-5-[1-(4-methoxyphenethyl)-2-pyrrolidinylmethyl]dibenzo[b,e][1,4]thiazepine (see Examples 1 and 6) (250 mg) in dichloromethane (10 ml) was stirred at room temperature for 16 hours and evaporated under reduced pressure. The residue was triturated with ether and the resulting solid collected, dried and recrystallised from ethyl acetate/hexane to give the title compound as colourless crystals, (250 mg, 83%), m.p. 151°–153° C., $[\alpha]_{589}^{25} -70.4°$ (c=0.575 in ethanol).

Analysis %: Found: C,72.1; H,6.7; N,4.7. $C_{27}H_{30}N_2OS \cdot C_8H_8O_3$: C,72.1; H,6.6; N,4.8.

EXAMPLE 26

(S)-5,11-Dihydro-5-[1-(4-methoxyphenethyl)-2-pyrrolidinylmethyl]dibenzo[b,e][1,4]thiazepine hydrochloride (1:1)

Excess saturated ethereal hydrogen chloride solution was added to a solution of (S)-5,11-dihydro-5-[1-(4-methoxyphenethyl)-2-pyrrolidinylmethyl]dibenzo[b-,e][1,4]thiazepine (see Examples 1 and 6) (1.30 g) in ether (20 ml) and the mixture was stirred at room temperature for 16 hours. The resulting precipitate was collected, washed several times with ether, dried and recrystallised from ethyl acetate to give the title compound as colourless crystals, (602 mg, 43%), m.p. 189°–190° C., $[\alpha]_{589}^{25} -30.7°$ (c=0.57 in ethanol).

Analysis %: Found: C,69.3; H,6.7; N,6.0. $C_{27}H_{30}N_2OS \cdot HCl$ requires: C,69.4; H,6.7; N,6.0.

EXAMPLE 27

(S)-5,11-Dihydro-5-[1-(2-[2-pyridyl]ethyl)-2-pyrrolidinylmethyl]dibenzo[b,e][1,4]thiazepine

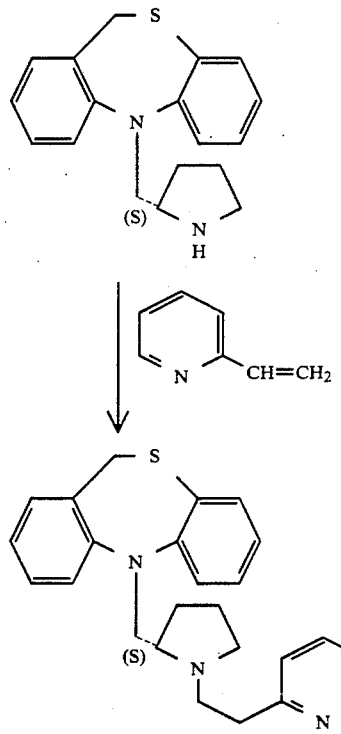

A mixture of 2-vinylpyridine (250 mg) and (S)-5,11-dihydro-5-(2-pyrrolidinylmethyl)dibenzo[b,e][1,4]-thiazepine (see Preparations 13 and 14) (166 mg) was heated at 120° C. for 2 hours, cooled to room temperature and purified by chromatography on silica gel using ethyl acetate/methanol (10:1) as eluant. Appropriate fractions were combined and evaporated under reduced pressure to give the title compound as a pale brown gum, (131 mg, 58%).

$^1$H-NMR (300 MHz, CDCl$_3$) δ=8.57 (d, 1H, J=8 Hz), 7.61 (dt, 1H, J=8 and 2 Hz), 6.90–7.40 (m, 10H), 6.80 (dt, 1H, J=8 and 2 Hz), 4.50–4.70 (broad s, 1H), 4.04 (dd, 2H, J=9 and 3 Hz) and 1.6–3.3 (m, 12H) ppm.

EXAMPLE 28

(2S)-5,11-Dihydro-5-[1-(4-methoxyphenethyl)-2-pyrrolidinylmethyl]dibenzo[b,e][1,4]thiazepine-10-oxide

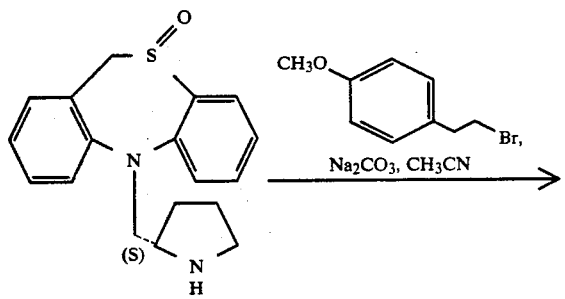

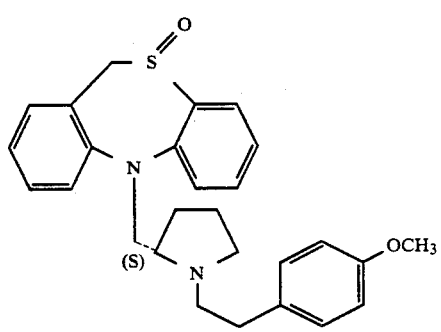

A mixture of (2S)-5,11-dihydro-5-(2-pyrrolidinylmethyl)dibenzo[b,e][1,4]thiazepine-10-oxide (see Preparation 19) (180 mg), 4-methoxyphenethyl bromide (140 mg) and sodium carbonate (70 mg) in acetonitrile (20 ml) was heated under reflux for 18 hours and evaporated under reduced pressure. The residue was partitioned between ethyl acetate and water and the organic layer washed with water, dried over sodium sulphate and evaporated under reduced pressure. The residue was purified by chromatography on silica gel (5 g), performing a gradient elution initially using dichloromethane as eluant and changing to dichloromethane/methanol (98:2). Appropriate fractions were combined and evaporated under reduced pressure to give the title compound as a colourless oil, (50 mg, 19%).

Analysis %: Found: C,70.7; H,6.7; N,6.0. $C_{27}H_{30}N_2O_2S.\tfrac{3}{4}H_2O$ requires: C,70.5; H,6.6; N,6.1.

EXAMPLE 29

(2S)-5,11-Dihydro-5-[1-(4-hydroxyphenethyl)-2-pyrrolidinylmethyl]dibenzo[b,e][1,4]thiazepine-10-oxide

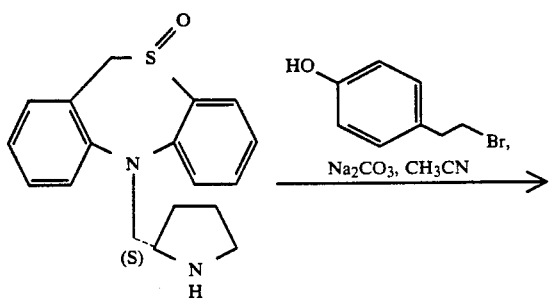

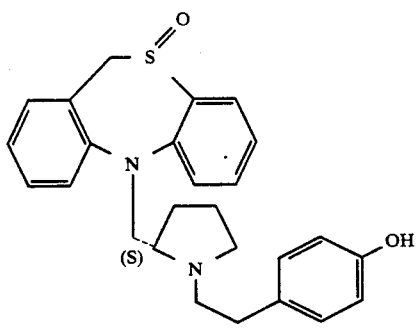

This was obtained by a similar method to that described in Example 28 using 4-hydroxyphenethyl bromide instead of 4-methoxyphenethyl bromide as the starting material. The title compound was obtained as a colourless oil, (50 mg, 26%).

Analysis %: Found: C,72.3; H,6.6; N,6.2. $C_{26}H_{28}N_2O_2S$ requires: C,72.2; H,6.5; N,6.5.

EXAMPLE 30

(S)-5,11-Dihydro-5-[1-(4-methoxyphenethyl)-2-pyrrolidinylmethyl]dibenzo[b,e][1,4]thiazepine-10,10-dioxide

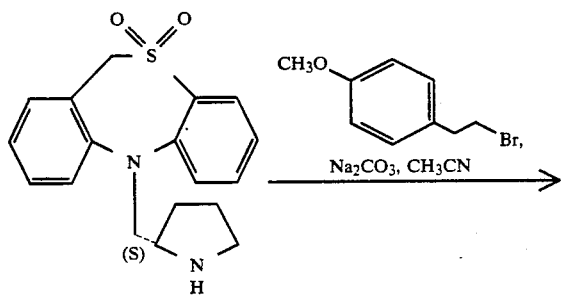

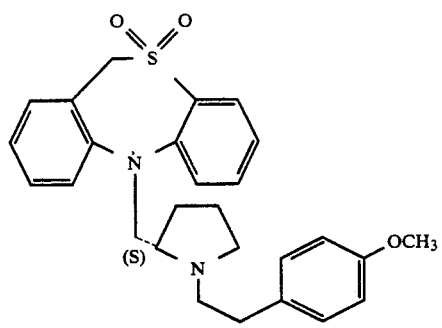

This was obtained by a similar method to that described in Example 28 using (S)-5,11-dihydro-5-(2-pyrrolidinylmethyl)dibenzo[b,e][1,4]thiazepine-10,10-dioxide (see Preparation 20) instead of (2S)-5,11-dihydro-5-(2-pyrrolidinylmethyl)dibenzo[b,e][1,4]thiazepine-10-oxide as the starting material. The title compound was obtained as a colourless oil, (80 mg, 28%).

Analysis %: Found: C,69.9; H,6.5; N,6.0. $C_{27}H_{30}N_2O_3S$ requires: C,70.1; H,6.5; N,6.1.

EXAMPLE 31

(S)-5,11-Dihydro-5-[1-(4-hydroxyphenethyl)-2-pyrrolidinylmethyl]dibenzo[b,e][1,4]thiazepine-10,10-dioxide

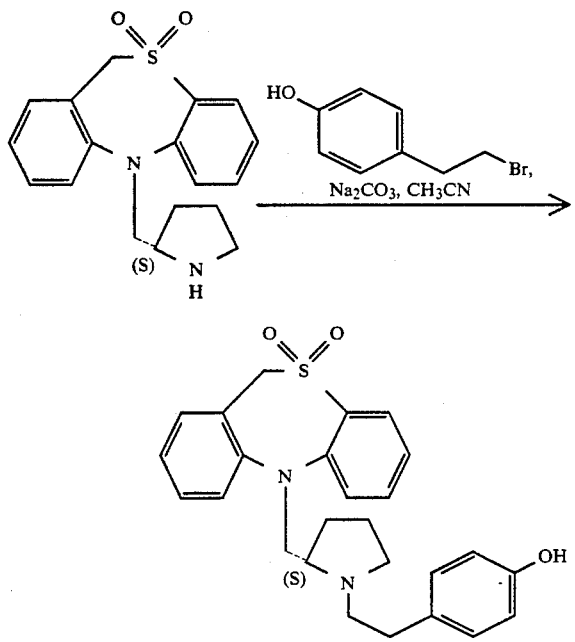

This was obtained by reacting (S)-5,11-dihydro-5-(2-pyrrolidinylmethyl)dibenzo[b,e][1,4]thiazepine-10,10-dioxide (see Preparation 20) and 4-hydroxyphenethyl bromide by a similar method to that described in Example 28. The title compound was obtained as a colourless oil, (60 mg, 29%).

Analysis %: Found: C,69.5; H,6.3; N,6.1. C$_{26}$H$_{28}$N$_2$O$_3$S requires: C,69.6; H,6.3; N,6.2.

The following Preparations illustrate the preparation of starting materials used in the preceding Examples:

PREPARATION 1

(R)-3-Chloro-1-(4-methoxyphenethyl)piperidine

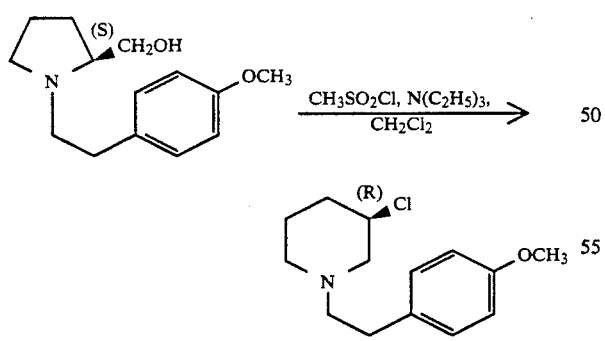

A mixture of methanesulphonyl chloride (1.3 ml), triethylamine (1.7 g) and (S)-2-hydroxymethyl-1-1(4-methoxyphenethyl)pyrrolidine (see Preparation 6) (4.0 g) in dichloromethane (30 ml) was stirred at room temperature for 2.5 hours, diluted with dichloromethane, washed with 10% aqueous sodium carbonate solution, dried over sodium sulphate and evaporated under reduced pressure to give the title compound as a pale brown oil, (4.0 g), which was characterised by NMR and used directly in Example 1 without further purification.

$^1$H-NMR (300 MHz, CDCl$_3$) δ=7.17 (d, 2H, J=8 Hz), 6.84 (d, 2H, J=8 Hz), 4.01-4.13 (m, 1H), 3.82 (s, 3H), 3.19 (d, 1H, J=14 Hz), 2.58-2.84 (m, 5H), 2.32 (t, 1H, J=14 Hz) and 1.6-2.3 (m, 4H) ppm.

PREPARATION 2

(S)-3-Chloro-1-(4-methoxyphenethyl)piperidine

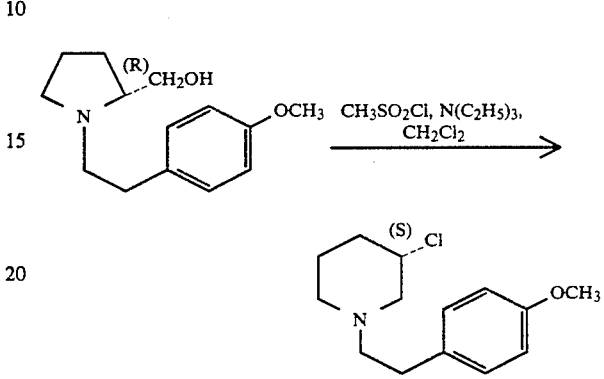

This was obtained by a similar method to that described in Preparation 1 using (R)-2-hydroxymethyl-1-(4-methoxyphenethyl)pyrrolidine (see Preparation 7) instead of (S)-2-hydroxymethyl-1-(4-methoxyphenethyl)pyrrolidine as the starting material. The title compound was obtained as a pale brown oil, (660 mg), which was characterised by NMR and used directly in Example 2 without further purification.

$^1$H-NMR (300 MHz, CDCl$_3$) δ=7.17 (d, 2H, J=8 Hz), 6.84 (d, 2H, J=8 Hz), 4.01-4.13 (m, 1H), 3.82 (s, 3H), 3.19 (d, 1H, J=14 Hz), 2.58-2.84 (m, 5H), 2.32 (t, 1H, J=14 Hz) and 1.6-2.3 (m, 4H) ppm.

PREPARATION 3

(R)-3-Chloro-1-(4-methoxyphenethyl)perhydroazepine

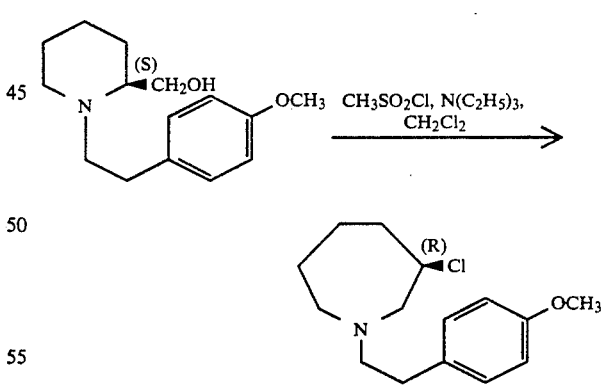

This was obtained by a similar method to that described in Preparation 1 using (S)-2-hydroxymethyl-1-(4-methoxyphenethyl)piperidine (see Preparation 8) instead of (S)-2-hydroxymethyl-1-(4-methoxyphenethyl)pyrrolidine as the starting material. The title compound was obtained as a pale brown oil, (2.6 g), which was characterised by NMR and used directly in Example 3 without further purification.

$^1$H-NMR (300 MHz, CDCl$_3$) δ=7.14 (d, 2H, J=8 Hz), 6.83 (d, 2H, J=8 Hz), 3.82 (s, 3H), 2.4-3.7 (m, 9H) and 1.6-1.8 (m, 6H) ppm.

PREPARATION 4

(S)-2-(2-Chloroethyl)-1-(4-methoxyphenethyl)pyrrolidine hydrochloride

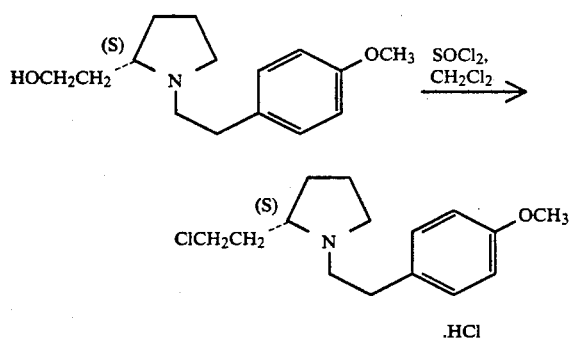

Thionyl chloride (2ml) was added slowly to a solution of (S)-2-(2-hydroxyethyl)-1-(4-methoxyphenethyl)-pyrrolidine (see Preparation 9) (3.0 g) in dichloromethane (30 ml). The mixture was heated under reflux for 2 hours and evaporated under reduced pressure to give the title compound as a brown oil, (4.15 g), which was characterised by NMR and used directly in Example 5 without further purification.

$^1$H-NMR (300 MHz, CDCl$_3$) δ=7.19 (d, 2H, J=8 Hz), 6.90 (d, 2H, J=8 Hz), 3.80–4.02 (m, 2H), 3.80 (s, 3H), 3.34–3.62 (m, 4H), 2.83–3.16 (m, 3H), 2.44–2.76 (m, 2H), 2.23–2.40 (m, 2H) and 1.98–2.16 (m, 2H) ppm.

PREPARATION 5

(R)-3-Chloro-1-(4-methoxyphenethyl)-3-methylpiperidine

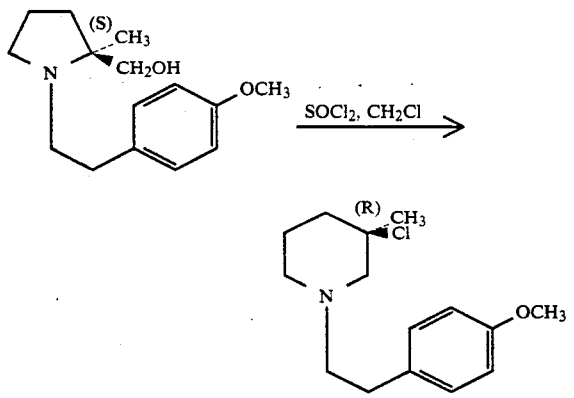

Thionyl chloride (238 mg) was added slowly to a solution of (S)-2-hydroxymethyl-1-(4-methoxyphenethyl)-2-methylpyrrolidine (see Preparation 10) (349 mg) in dichloromethane (15 ml) and the mixture was heated under reflux for 2 hours. The reaction was cooled, diluted with dichloromethane, washed with 10% aqueous sodium carbonate solution, dried over sodium sulphate and evaporated under reduced pressure to give the title compound as a brown gum, (130 mg), which was characterised by NMR and used directly in Example 4 without further purification.

$^1$H-NMR (300 MHz, CDCl$_3$) δ=7.19 (d, 2H, J=8 Hz), 6.82 (d, 2H, J=8 Hz), 3.80 (s, 3H), 2.2–3.1 (m, 8H), 1.62 (s, 3H) and 1.4–2.1 (m, 4H) ppm.

PREPARATION 6

(S)-2-Hydroxymethyl-1-(4-methoxyphenethyl)pyrrolidine

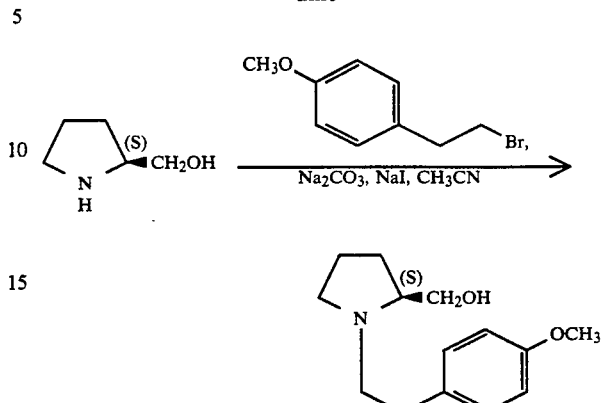

A mixture of (S)-2-pyrrolidinemethanol (3.0 g), 4-methoxyphenethyl bromide (7.0 g), sodium carbonate (3.5 g) and sodium iodide (100 mg) in acetonitrile (40 ml) was heated under reflux for 16 hours and evaporated under reduced pressure. The residue was partitioned between ethyl acetate and water and the organic layer washed with water and extracted with 2M hydrochloric acid. The acidic extract was washed with ethyl acetate, basified with solid sodium carbonate and extracted with ethyl acetate. The organic extract was dried over sodium sulphate and evaporated under reduced pressure to give the title compound as a colourless oil, (4.0 g, 57%).

$^1$H-NMR (300 MHz, CDCl$_3$) δ=7.16 (d, 2H, J=8 Hz), 6.83 (d, 2H, 8 Hz), 3.81 (s, 3H), 3.59 (dd, 1H, J=8 and 2 Hz), 3.26–3.40 (m, 2H), 2.3–3.1 (m, 7H) and 1.6–2.0 (m, 4H) ppm.

PREPARATION 7

(R)-2-Hydroxymethyl-1-(4-methoxyphenethyl)pyrrolidine

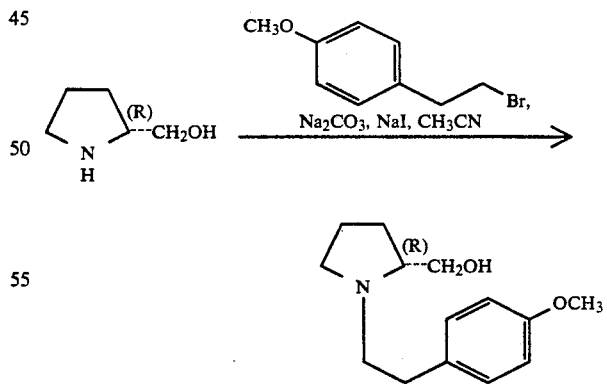

this was obtained by a similar method to that described in Preparation 6 using (R)-2-pyrrolidinemethanol instead of (S)-2-pyrrolidinemethanol as the starting material. The title compound was obtained as a pale brown oil, (1.8 g, 77%), [α]$_{589}^{25}$ +68.9° (c=1.5 in ethanol).

Analysis %: Found: C,70.9; H,9.0; N,5.9. C$_{14}$H$_{21}$NO$_2$.¼ H$_2$O requires: C,70.1; H,8.8; N,5.8.

PREPARATION 8

(S)-2-Hydroxymethyl-1-(4-methoxyphenethyl)piperidine

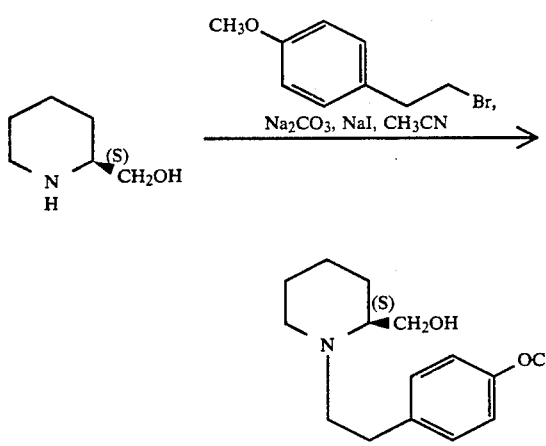

This was obtained by a similar method to that described in Preparation 6 using (S)-2-piperidinemethanol (prepared by resolution of racemic 2-piperidinemethanol as described in Japan Kokai 73 19,597—see Chem. Abs.,78, 148000f (1973)) instead of (S)-2-pyrrolidinemethanol as the starting material. The title compound was obtained as a colourless oil, (4.8 g, 64%), $[\alpha]_{589}^{25} - 39.3°$ (c=1.025 in ethanol).

$^1$H-NMR (300 MHz, CDCl$_3$) $\delta$=7.16 (d, 2H, J=8 Hz), 6.83 (d, 2H, J=8 Hz), 3.80 (s, 3H), 3.76 (dd, 1H, J=9 and 3 Hz), 3.63 (dd, 1H, J=9 and 2 Hz), 2.3–3.1 (m, 9H) and 1.3–1.8 (m, 4H) ppm.

PREPARATION 9

(S)-2-(2-Hydroxyethyl)-1(4-methoxyphenethyl)pyrrolidine

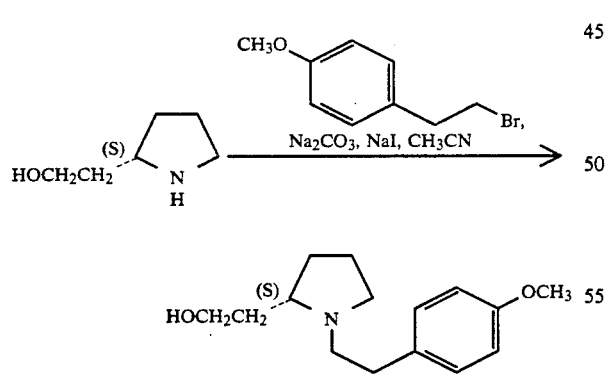

This was obtained by a similar method to that described in Preparation 6 using (S)-2-(2-hydroxyethyl)-pyrrolidine (see Preparation 11) instead of (S)-2-pyrrolidinemethanol as the starting material. The title compound was obtained as a colourless oil, (4.7 g, 68%), $[\alpha]_{589}^{25} - 80.4°$ (c=1.0 in methanol).

Analysis %: Found: C,70.7; H,9.3; N,5.5. C$_{15}$H$_{23}$NO$_2 \cdot \frac{1}{4}$H$_2$O requires: C,71.0; H,9.3; N,5.5.

PREPARATION 10

(S)-2-Hydroxymethyl-1-(4-methoxyphenethyl)-2-methylpyrrolidine

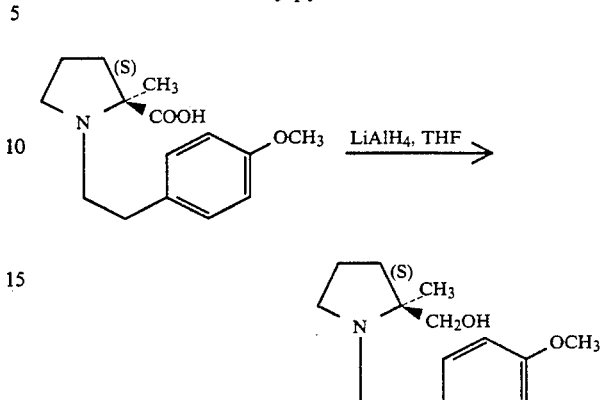

(S)-1-(4-Methoxyphenethyl)-2-methylproline (see Preparation 12) (895 mg) was added portionwise to a stirred suspension of lithium aluminium hydride (380 mg) in tetrahydrofuran (60 ml) and the mixture stirred at room temperature for 22 hours. The reaction was quenched by the cautious, dropwise, sequential addition of water (0.4 ml), 5M aqueous sodium hydroxide solution (0.4 ml) and water (1.2 ml), and then the resulting mixture filtered. The filtrate was dried over sodium sulphate and evaporated under reduced pressure to give the title compound as a colourless oil, (390 mg, 46%).

$^1$H-NMR (300 MHz, CDCl$_3$) $\delta$=7.16 (d, 2H, J=8 Hz), 6.84 (d, 2H, J=8 Hz), 3.81 (s, 3H), 3.37 (dt, 1H, J=2 and 8 Hz), 3.21 (q, 2H, J=7 Hz), 2.4–3.1 (m, 5H), 1.98–2.11 (m, 1H), 1.66–1.86 (m, 2H), 1.42–1.58 (m, 1H) and 0.84 (s, 3H) ppm.

PREPARATION 11

(S)-2-(2-Hydroxyethyl)pyrrolidine

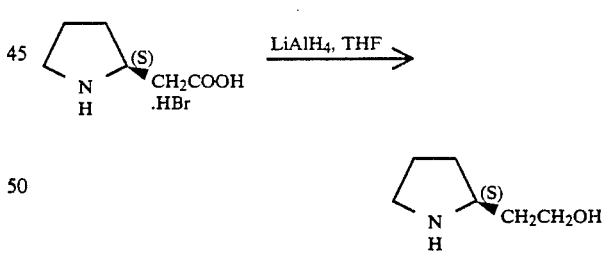

Lithium aluminium hydride (3.27 g) was added, portionwise over 30 minutes, to a stirred suspension of (S)-2-pyrrolidineacetic acid hydrobromide (7.23 g) (prepared by the method of R. Busson and H. Vanderhaeghe, J. Org. Chem., 43, 4438 (1978)) in tetrahydrofuran (240 ml) and the mixture heated under reflux for 3.5 hours. The reaction was allowed to cool to room temperature, quenched by the cautious, dropwise, sequential addition of water (3 ml), 2M aqueous sodium hydroxide solution (3 ml) and water (2 ml), treated with sodium sulphate (10 g) and filtered. The filtrate was evaporated under reduced pressure to give the title compound as a colourless oil, (3.2 g, 81%) $[\alpha]_{589}^{25} - 25.1°$ (c=1.0 in methanol).

¹H-NMR (300 MHz, CDCl₃) δ=3.78 (dt, 2H, J=7 and 3 Hz), 3.68 (broad s, 2H), 3.37-3.47 (m, 1H), 2.89 (t, 2H, J=7 Hz) and 1.4-2.2 (m, 6H) ppm.

PREPARATION 12

(S)-1-(4-Methoxyphenethyl)-2-methylproline

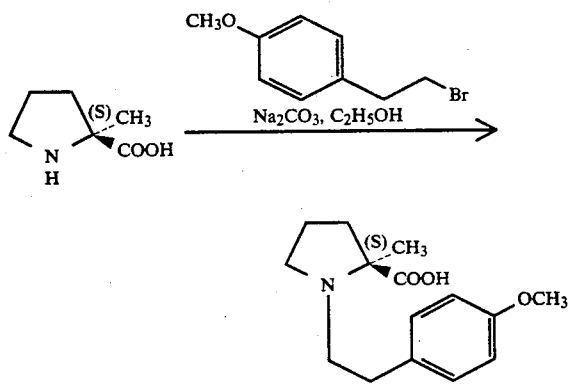

A mixture of (S)-2-methylproline (1.47 g) (prepared by the method of D. Seebach et al., JACS, 105, 5390 (1983)), 4-methoxyphenethyl bromide (1.72 g) and sodium carbonate (2.12 g) in ethanol (30 ml) was heated under reflux for 48 hours, adjusted to pH8 with 2M hydrochloric acid, treated with glacial acetic acid to pH7, filtered and evaporated under reduced pressure. The residue was triturated with ethanol, filtered and evaporated under reduced pressure to give the title compound as a brown gum, (1.55 g), which was used directly in Preparation 10 without further purification.

PREPARATION 13

(S)-5,11-Dihydro-5-(2-pyrrolidinylmethyl)dibenzo[b,e][1,4]thiazepine

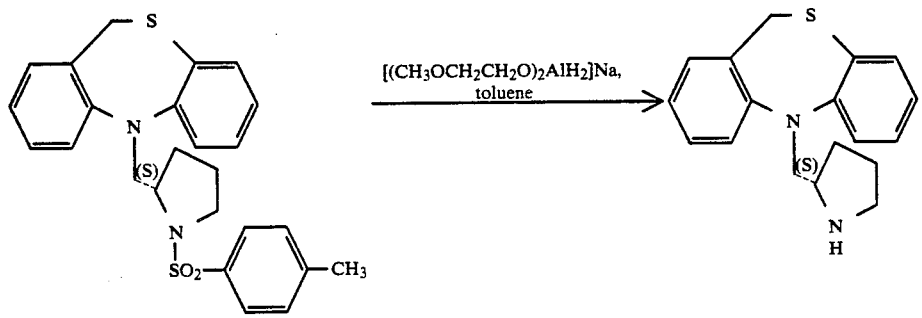

Sodium bis(2-methoxyethoxy)aluminium hydride ("Red-Al"-registered Trade Mark) (20.8 ml of a 3.4M solution in toluene) was added to a solution of (S)-5,11-dihydro-5-(1-[4-methylphenylsulphonyl]-2-pyrrolidinylmethyl)dibenzo[b,e][1,4]thiazepine (see Preparations 15 and 16) (8.0 g) in toluene (50 ml) and the mixture heated under reflux for 27 hours, allowed to cool to room temperature, quenched by the addition of 2.5M aqueous sodium hydroxide solution, diluted with water and extracted with ethyl acetate. The combined organic extracts were washed with saturated aqueous sodium chloride solution, dried over sodium sulphate and evaporated under reduced pressure. The residue was purified by chromatography on silica gel, performing a gradient elution initially using dichloromethane as eluant and changing to dichloromethane/saturated methanolic ammonia (90:10). Appropriate fractions were combined and evaporated under reduced pressure to give the title compound as a colourless oil, (2.9 g, 55%), $[\alpha]_{589} -4.9°$ (c=1.065 in ethanol).

¹H-NMR (300 MHz, CDCl₃) δ=7.0-7.4 (m, 7H), 6.84 (t, 1H, J=8 Hz), 4.1-4.7 (broad s, 2H), 3.96 (dd, 1H, J=10 and 4 Hz), 3.66 (dd, 1H, J=10 and 5 Hz), 3.0-3.5 (m, 3H) and 1.6-2.1 (m, 4H) ppm.

PREPARATION 14

(S)-5,11-Dihydro-5-(2-pyrrolidinylmethyl)dibenzo[b,e][1,4]-thiazepine

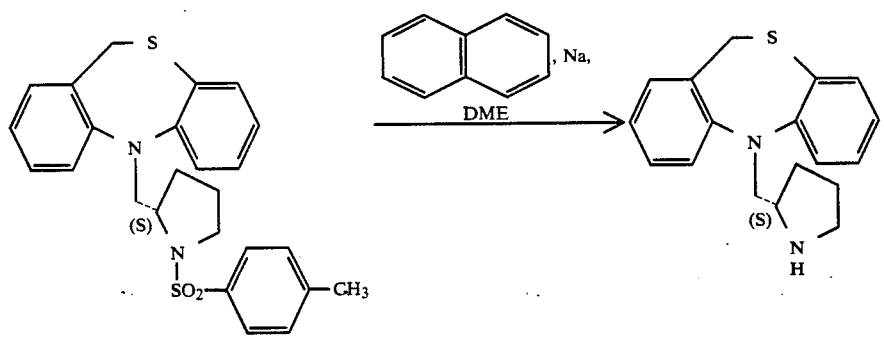

Sodium (55 mg) was added to a solution of naphthalene (340 mg) in DME (6 ml) and the mixture stirred at room temperature for one hour, treated with a solution of (S)-5,11-dihydro-5-(1-[4-methylphenylsulphonyl]-2-pyrrolidinylmethyl)dibenzo[b,e][1,4]thiazepine (see Preparations 15 and 16) (200 mg) in DME (4 ml), stirred with ice-cooling for one hour, quenched with water and extracted with ethyl acetate. The organic extract was worked-up and purified as described in Preparation 13 to give the title compound as a colourless oil, (16 mg, 12%).

¹H-NMR (300 MHz, CDCl₃) δ=7.0-7.4 (m, 7H), 6.84 (t, 1H, J=8 Hz), 4.1-4.7 (broad s, 2H), 3.96 (dd, 1H, J=10 and 4 Hz), 3.66 (dd, 1H, J=10 and 5 Hz), 3.0-3.5 (m, 3H) and 1.6-2.1 (m, 4H) ppm.

PREPARATION 15

(S)-5,11-Dihydro-5-(1-[4-methylphenylsulphonyl]-2-pyrrolidinylmethyl)dibenzo[b,e][1,4]thiazepine acetate. The organic extract was washed with water, dried over sodium sulphate and evaporated under reduced pressure. The residue was purified by chromatography on silica gel, performing a gradient elution initially using hexane as eluant and changing to hexane/ethyl acetate (90:10). Appropriate fractions were combined and evaporated under reduced pressure to give the title compound as a colourless solid, (0.93 g, 44%), m.p. 88°-90° C., $[\alpha]_{589}^{25}$ −115° (c=0.62 in ethanol).

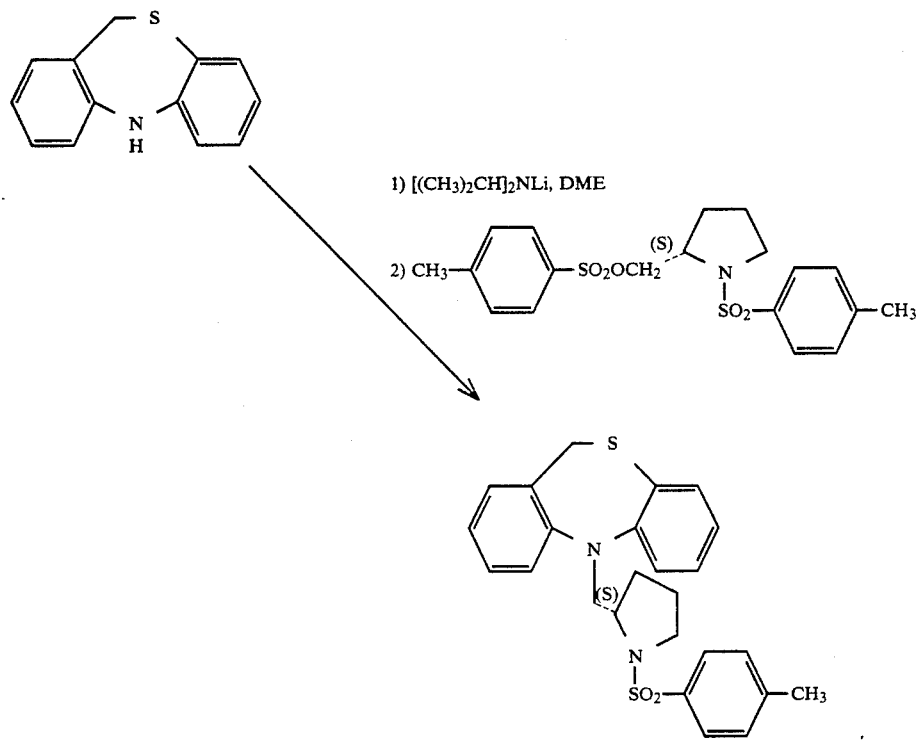

Lithium diisopropylamide (4.3 ml of a 1.5M solution in hexane) was added to a solution of 5,11-dihydrodibenzo[b,e][1,4]thiazepine (see Example 1 for source) (1.0 g) in DME (25 ml) and the mixture stirred at room temperature for 15 minutes, treated with (S)-1-(4-methylphenylsulphonyl)-2-(4-methylphenylsulphonyloxymethyl)pyrrolidine (3.9 g) (prepared by the method of P. Karrer and K. Ehrhardt, Helv. Chim. Acta, 34, 2202 (1951)), heated under reflux for 2.5 hours, allowed to cool to room temperature, quenched with 2M hydrochloric acid and extracted with ethyl ¹H-NMR (300 MHz, CDCl₃) δ=6.9-7.6 (m, 12H), 4.6 (dd, 2H, J=8 Hz and 2 Hz), 4.2-4.4 (broad, 1H), 3.5 (m, 2H), 3.0-3.2 (m, 2H), 2.42 (s, 3H), 2.0 (m, 1H), 1.8 (m, 1H), 1.6 (m, 2H) ppm.

Analysis %: Found: C,66.9; H,6.2; N,5.9: C₂₅H₂₆N₂O₂S₂ requires: C,66.6; H,5.8; N,6.2.

PREPARATION 16

(S)-5,11-Dihydro-5-(1-[4-methylphenylsulphonyl]-2-pyrrolidinylmethyl)dibenzo[b,e][1,4]thiazepine

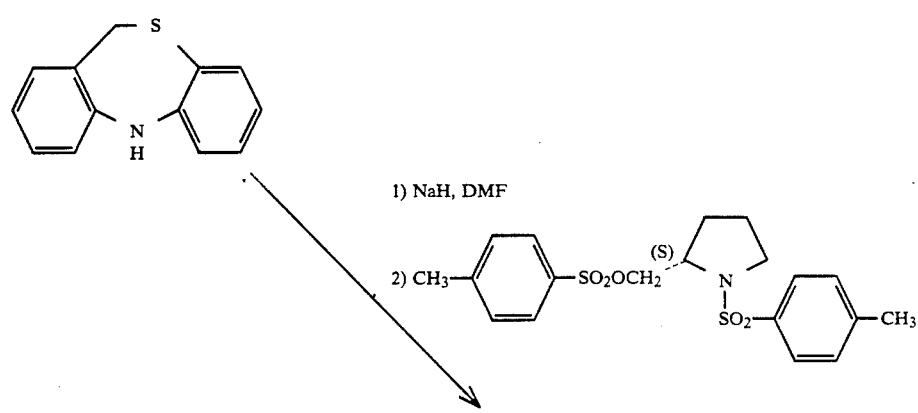

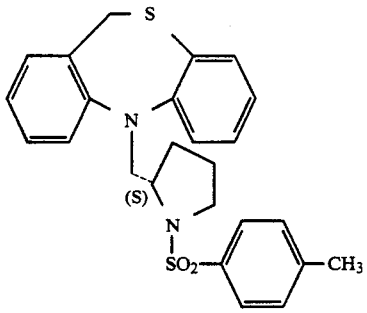

Sodium hydride (80% dispersion in oil, 40 mg) was added to a solution of 5,11-dihydrodibenzo[b,e][1,4]-thiazepine (see Example 1 for source) (213 mg) in dimethylformamide (10 ml) and the mixture heated at 60° C. for 45 minutes, treated with a solution of (S)-1-(4-methylphenylsulphonyl)-2-(4-methylphenylsulphonyloxymethyl)pyrrolidine (see Preparation 15 for source) (440 mg) in dimethylformamide (5 ml), heated at 60° C. for 7 hours and evaporated under reduced pressure. The residue was partitioned between ethyl acetate and water and the organic layer washed with water, dried over sodium sulphate and evaporated under reduced pressure. The residue was purified by chromatography on silica gel, performing a gradient elution initially using hexane as eluant and changing to hexane/ethyl acetate (60:40). Appropriate fractions were combined and evaporated under reduced pressure to give the title compound as a colourless oil, (50 mg, 24%).

$^1$H-NMR (300 MHz, CDCl$_3$) δ=6.9–7.6 (m, 12H), 4.6 (dd, 2H, J=8 Hz and 2 Hz), 4.2–4.4 (broad, 1H), 3.5 (m, 2H), 3.0–3.2 (m, 2H), 2.42 (s, 3H), 2.0 (m, 1H), 1.8 (m, 1H), 1.6 (m, 2H) ppm.

PREPARATION 17

5-(2-Bromoethyl)indane

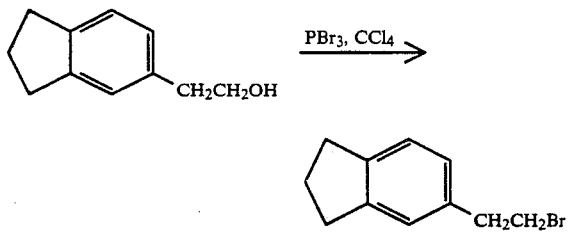

Phosphorous tribromide (3.5 ml) was added dropwise to an ice-cooled solution of 5-(2-hydroxyethyl)indane (14.0 g) (prepared as described in FR-2,139,628 (14.0 g) in carbon tetrachloride (100 ml) and the mixture was heated under reflux for 2 hours, quenched with ice-water and partitioned between dichloromethane and 10% aqueous sodium carbonate solution. The organic layer was washed with water, dried over magnesium sulphate and evaporated under reduced pressure. The residue was purified by chromatography on silica gel using dichloromethane as eluant. Appropriate fractions were combined and evaporated under reduced pressure to give the title compound as a pale yellow oil, (10.5 g, 54%).

$^1$H-NMR (300 MHz, CDCl$_3$) δ=7.20 (dd, 1H, J=8 and 1.5 Hz), 7.10 (d, 1H, J=1.5 Hz), 6.99 (d, 1H, J=8Hz), 3.58 (t, 2H, J=7 Hz), 3.17 (t, 2H, J=7 Hz), 2.80–3.02 (m, 4H) and 2.02–2.18 (m, 2H) ppm.

PREPARATION 18

4-(2-[Methanesulphonyloxy]ethyl)pyrimidine

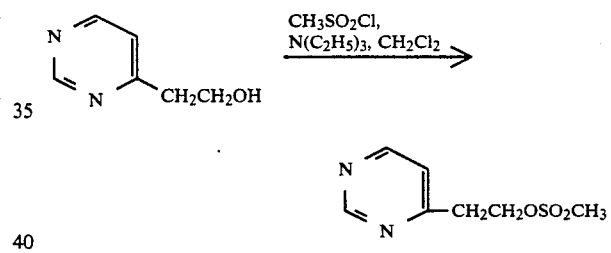

A solution of methanesulphonyl chloride (137 mg) in dichloromethane (2 ml) was added to a solution of 4-(2-hydroxyethyl)pyrimidine (124 mg) (prepared by the method of C. G. Overberger and I. C. Kogon, JACS, 76, 1879 (1954)) and triethylamine (121 mg) in dichloromethane (10 ml), the mixture stirred at room temperature for 3 hours and evaporated under reduced pressure to give the crude title compound as a pale yellow oil which was used directly in Example 10 without further purification.

PREPARATION 19

(2S)-5,11-Dihydro-5-(2-pyrrolidinylmethyl)dibenzo[b,e][1,4]thiazepine-10-oxide

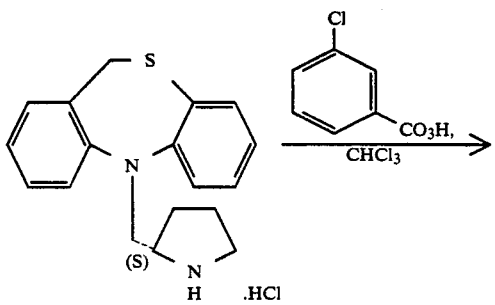

-continued

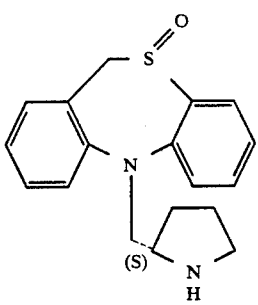

A solution of meta-chloroperbenzoic acid (105 mg) in chloroform (5 ml) was added to a solution of (S)-5,11-dihydro-5-(2-pyrrolidinylmethyl)dibenzo[b,e][1,4]-thiazepine hydrochloride (see Preparation 21) (200 mg) in chloroform (10 ml) and the mixture stirred at room temperature for 4 hours, washed with 10% aqueous sodium carbonate solution, dried over sodium sulphate and evaporated under reduced pressure to give the title compound as a colourless gum, (180 mg, 96%).

$^1$H-NMR (300 MHz, CDCl$_3$) δ=7.78 (dd, 1H, J=8 and 2 Hz), 7.0-7.6 (m, 7H), 4.30-4.62 (m, 2H), 3.63-3.80 (m, 2H), 3.24 (sextet, 1H, J=7 Hz), 2.81-3.02 (m, 2H) and 1.4-2.0 (m, 5H) ppm.

PREPARATION 20

(S)-5,11-Dihydro-5-(2-pyrrolidinymethyl)dibenzo[b,e][1,4]thiazepine-10,10-dioxide

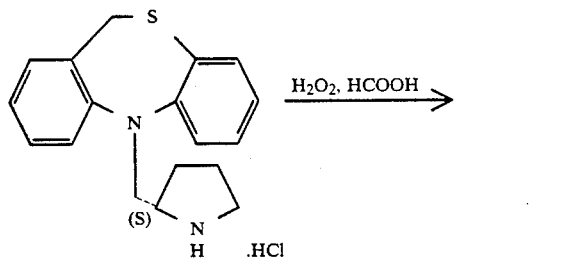

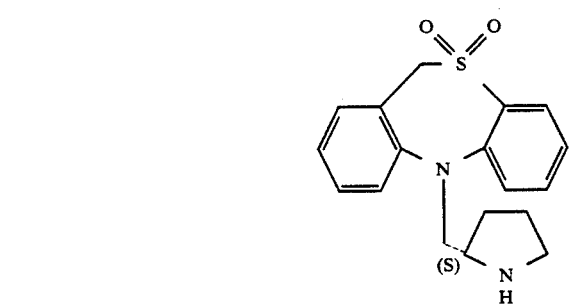

Hydrogen peroxide (30 wt. % solution in water, 0.8 ml) was added to a hot (85° C.) solution of (S)-5,11-dihydro-5-(2-pyrrolidinylmethyl)dibenzo[b,e][1,4]-thiazepine hydrochloride (see Preparation 21) (660 mg) in formic acid (5 ml) and the mixture heated at 90°-95° C. for 2 hours, poured into water, basified with solid sodium hydroxide to pH 10 and extracted with ethyl acetate. The combined organic extracts were dried over sodium sulphate and evaporated under reduced pressure to give the title compound as a pale brown solid, (540 mg, 91%), which was used directly in Examples 30 and 31.

PREPARATION 21

(S)-5,11-Dihydro-5-(2-pyrrolidinylmethyl)dibenzo[b,e][1,4]thiazepine hydrochloride (1:1)

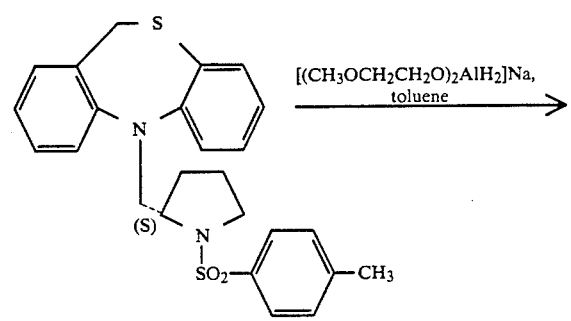

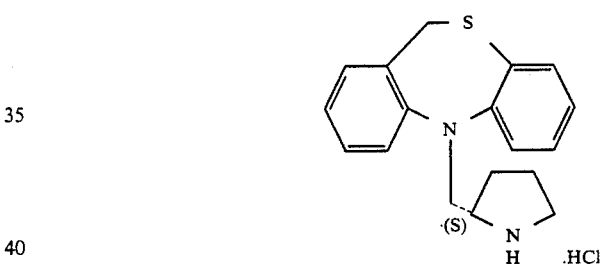

A mixture of (S)-5,11-dihydro-5-[1-(4-methylphenylsulphonyl)-2-pyrrolidinylmethyl]dibenzo[b,e][1,4]-thiazepine (see Preparations 15 and 16) (77.6 g) and sodium bis(2-methoxyethoxy)aluminium hydride ("Red-Al"-registered Trade Mark) (202 ml of a 3.4M solution in toluene) in toluene (202 ml) was heated under reflux for 17 hours, allowed to cool to room temperature, poured cautiously into a mixture of 2.5M aqueous sodium hydroxide solution (400 ml) and ether (200 ml) and the layers separated. The aqueous layer was extracted twice with ether and the combined organic layers extracted twice with 3M hydrochloric acid. The combined acidic extracts were stirred at room temperature for 18 hours and the resulting precipitate collected, stirred with water (200 ml), filtered and dried to give the title compound as a colourless solid, (22.4 g, 39%), m.p. 155°-160° C. (decomp.).

Analysis %: Found: C,63.4; H,6.9; N,8.0. C$_{18}$H$_{20}$N$_2$S.HCl.½ H$_2$O requires: C,63.2; H,6.5; N,8.2.

PREPARATION 22

(2S)-(N-[2-(2-Bromophenylmethylthio)phenyl]-)aminomethyl-1-(4-methoxyphenethyl)pyrrolidine

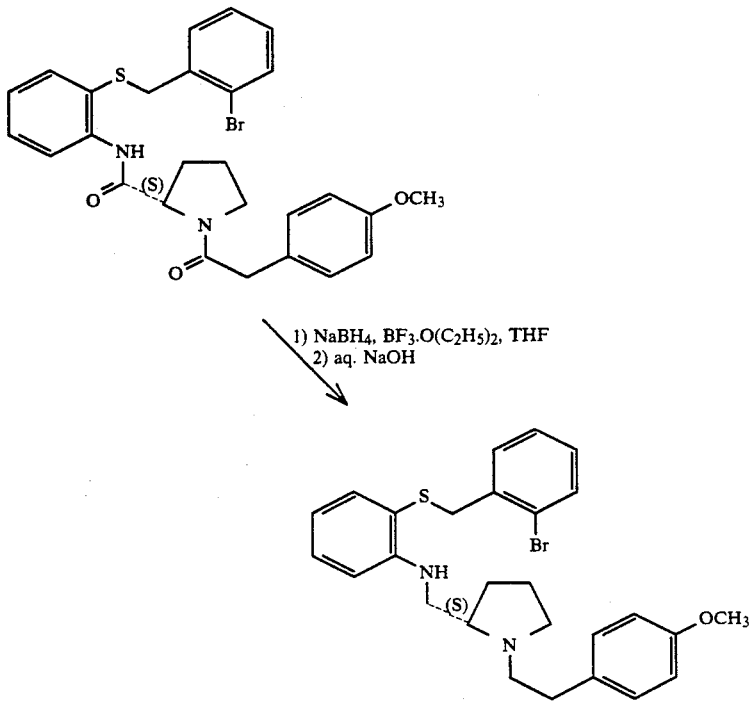

Boron trifluoride etherate (1531 g, 1327 ml) was added over ten minutes to a stirred, ice-cooled solution of (2S)-(N-[2-(2-bromophenylmethylthio)phenyl])carbamoyl-1-(4-methoxyphenylacetyl)pyrrolidine (see Preparation 23) (1750 g) and sodium borohydride (306.2 g) in tetrahydrofuran (8.73 L). The mixture was stirred at room temperature for one hour, heated under reflux for two hours, cooled, evaporated under reduced pressure to reduced volume to remove the tetrahydrofuran, quenched by the cautious addition of water and further evaporated under reduced pressure. The residue was treated with 40% aqueous sodium hydroxide solution (5 L) and the mixture was heated under reflux for two hours, cooled to room temperature by the addition of ice, acidified to pH 6-7 with concentrated hydrochloric acid and extracted with dichloromethane. The combined organic extracts were washed with 1M aqueous sodium hydroxide solution followed by water, dried over magnesium sulphate and evaporated under reduced pressure to give the desired compound (1589 g, 96%) as a brown oil which was characterised by $^1$H-NMR spectroscopy.

$^1$H-NMR (CDCl$_3$) $\delta$=7.56 (d, 1H, J=8 Hz), 7.00-7.15 (m, 6H), 6.93 (d, 1H, J=8 Hz), 6.81 (d, 2H, J=8 Hz), 6.50-6.61 (m, 2H), 5.54 (broad s, 1H), 3.99 (s, 2H), 3.75 (s, 3H), 2.70-3.40 (m, 7H), 2.44-2.57 (m, 1H), 2.30-2.40 (m, 1H), 1.65-2.03 (m, 4H) ppm.

PREPARATION 23

(2S)-(N-[2-(2-Bromophenylmethylthio)phenyl])carbamoyl-1-(4-methoxyphenylacetyl)pyrrolidine

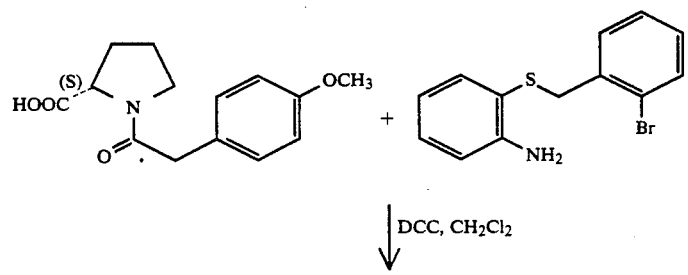

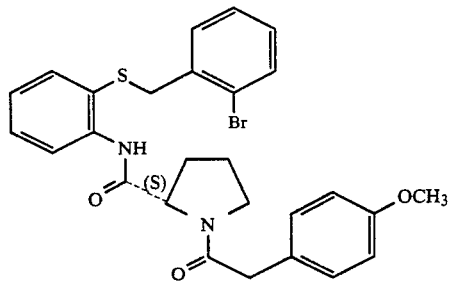

15

A solution of 1,3-dicyclohexylcarbodiimide (DCC) (705 g) in dichloromethane (1400 ml) was added over 30 minutes to a stirred solution of 2-(2-bromophenylmethylthio)aniline (see Bull. Chem. Soc. Japan, 48, 2323 (1975)) (957 g) and (S)-1-(4-methoxyphenylacetyl)proline (see Preparation 24) (900 g) in dichloromethane (5.5 L). The mixture was stirred at 25°–35° C. for one hour and filtered. The filtrate was evaporated under reduced pressure to give the desired product as a brown gum which was used directly in Preparation 22.

PREPARATION 24

(S)-1-(4-Methoxyphenylacetyl)proline

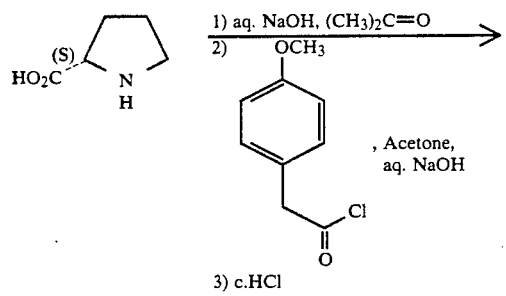

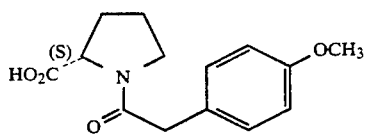

5M Aqueous sodium hydroxide solution (26 ml) was added to a solution of (S)-proline (582 g) in water (3.5 L) and acetone (3.5 L). The mixture was treated with ice (3.5 kg), cooled in an ice/acetone bath, treated over a one hour period with a solution of 4-methoxyphenylacetyl chloride (944 g) in acetone (1.75 L) with vigorous stirring and the simultaneous addition of sufficient 5M aqueous sodium hydroxide solution in order to keep the pH within the range 9.5–9.7. The reaction was stirred for 30 minutes, treated with concentrated hydrochloric acid (6 ml) and partially evaporated under reduced pressure to remove the majority of the acetone. The residue was treated with ice (2 kg), concentrated hydrochloric acid (750 ml) and the mixture stirred at room temperature for one hour. The resulting precipitate was collected, washed with water and recrystallised from toluene/ethanol to give the desired product as a colourless solid (905 g, 75%), m.p. 138°–139° C.

Analysis %: Found: C,63.6; H,6.5; N,5.2. $C_{14}H_{17}NO_4$ requires: C,63.9; H,6.5; N,5.3.

PREPARATION 25

5,11-Dihydro-5-[1-(4-methoxyphenylacetyl)-2-pyrrolidinylcarbonyl]dibenzo[b,e][1,4]thiazepine

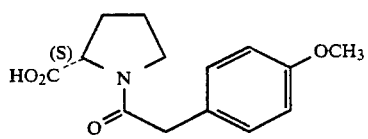

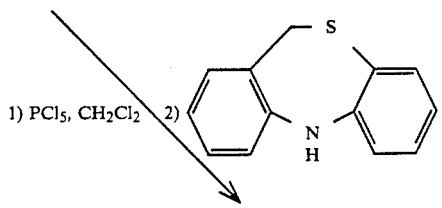

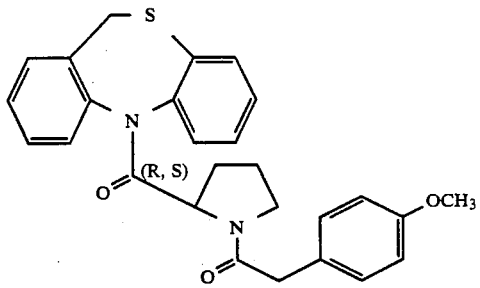

A solution of phosphorus pentachloride (20.8 g) in dichloromethane (100 ml) was added over 5 minutes to a stirred solution of (S)-1-(4-methoxyphenylacetyl)proline (see Preparation 24) (26.33 g) in dichloromethane (150 ml). The mixture was stirred at room temperature for one hour, treated with a solution of 5,11-dihydrodibenzo[b,e][1,4]thiazepine (see Example 1 for source) (21.3 g) in dichloromethane (100 ml) and heated under reflux for 2 hours. The mixture was treated with toluene (300 ml) and the mixture was heated under reflux whilst distilling off a portion of the dichloromethane until the reflux temperature of the mixture was about 60° C. The mixture was heated under reflux for a further 4 hours, cooled, washed with saturated aqueous sodium bicarbonate solution, dried over magnesium sulphate and evaporated under reduced pressure. The residue was purified by column chromatography on silica using dichloromethane as the eluant. The appropriate fractions were combined and evaporated under reduced pressure to give the crude product (32.5 g, 71%), which was used directly in Example 21.

We claim:

1. A compound of the formula:

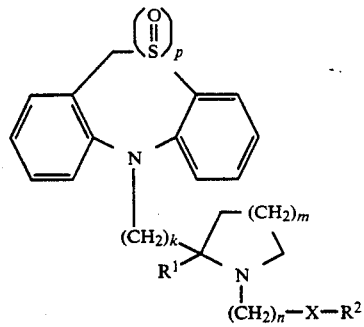

(I)

wherein
k is 1, 2 or 3;
m is 1, 2 or 3;
n is 1, 2 or 3;
p is 0, 1 or 2;
X is O, S or a direct link, with the proviso that when X is O or S, n is 2 or 3;
$R^1$ is H or $C_1$-$C_4$ alkyl; and
$R^2$ is
   (a)

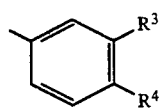

wherein $R^3$ and $R^4$ are each independently selected from H, $C_1$-$C_4$ alkyl, $C_1$-$C_4$ alkoxy, —OH and halo;

(b)

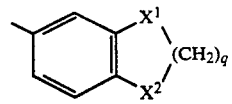

wherein $R^3$ and $R^4$ are each independently selected from H, $C_1$-$C_4$ alkyl, $C_1$-$C_4$ alkoxy, —OH, —N($C_1$-$C_4$ alkyl)$_2$, halo and —$CF_3$;

(b)

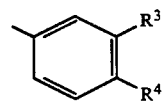

wherein q is 1, 2 or 3, and $X^1$ and $X^2$ are each independently selected from 0 and —$CH_2$—; or
(c) a pyridinyl, pyridazinyl, pyrimidinyl, pyrazinyl or thienyl group, said group being optionally substituted by up to 2 substituents each independently selected from $C_1$-$C_4$ alkyl and $C_1$-$C_4$ alkoxy, or a pharmaceutically acceptable salt thereof.

2. A compound of the formula (I) as claimed in claim 1 wherein k is 1 or 2.

3. A compound of the formula (I) as claimed in claim 2 wherein k is 1.

4. A compound of the formula (I) as claimed in claim 1 wherein m is 1 or 2.

5. A compound of the formula (I) as claimed in claim 4 wherein m is 1.

6. A compound of the formula (I) as claimed in claim 1 wherein n is 2.

7. A compound of formula (I) as claimed in claim 1 wherein p is 0.

8. A compound of the formula (I) as claimed in claim 1 wherein X is a direct link.

9. A compound of the formula (I) as claimed in claim 1 wherein $R^1$ is H or methyl.

10. A compound of the formula (I) as claimed in claim 9 wherein $R^1$ is H.

11. A compound of the formula (I) as claimed in claim 1 wherein $R^2$ is
   (a)

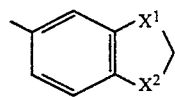

wherein $X^1$ and $X^2$ are as defined in claim 1; or (c) a pyridinyl, pyrimidinyl or thienyl group, said group being optionally substituted by up to 2 substituents each independently selected from $C_1$–$C_4$ alkyl and $C_1$–$C_4$ alkoxy.

12. A compound of the formula (I) as claimed in claim 11 wherein $R^2$ is phenyl, 3-methylphenyl, 4-methylphenyl, 4-hydroxyphenyl, 4-methoxyphenyl, 3,4-dimethoxyphenyl, 4-chlorophenyl, 5-indanyl, 3,4-methylenedioxyphenyl, 2-pyridinyl, 4-pyrimidinyl or 3-thienyl.

13. A compound of the formula (I) as claimed in claim 12 wherein $R^2$ is 4-methoxyphenyl.

14. A (2S)-stereoisomer of a compound of the formula (I) as claimed in claim 1, that is

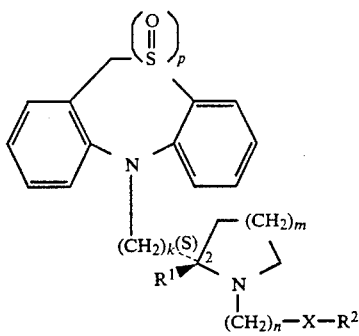

15. (S)-5,11-Dihydro-5-[1-(4-methoxyphenethyl)-2-pyrrolidinylmethyl]dibenzo[b,e][1,4]thiazepine or a pharmaceutically acceptable salt thereof.

16. A maleate salt of a compound of the formula (I) as claimed in claim 1.

17. A pharmaceutical composition comprising a compound of the formula (I), or a pharmaceutically acceptable salt thereof, as claimed in claim 1, together with a pharmaceutically acceptable diluent or carrier.

18. A method of treating a mammal afflicted with a motility disorder, particularly of the gut such as irritable bowel syndrome, which comprises treating said animal with an effective amount of a compound of the formula (I), or with, as appropriate, a pharmaceutically acceptable salt or composition thereof, as claimed in claim 1.

* * * * *